US012697087B2

(12) United States Patent
Marcolino Quintao Severgnini et al.

(10) Patent No.: US 12,697,087 B2
(45) Date of Patent: Aug. 4, 2026

(54) HEART RATE DETECTION ASSEMBLY AND METHODS OF DETECTING A HEART RATE

(71) Applicant: Toyota Motor Engineering & Manufacturing North America, Inc., Plano, TX (US)

(72) Inventors: Frederico Marcolino Quintao Severgnini, Ann Arbor, MI (US); Ercan Mehmet Dede, Ann Arbor, MI (US)

(73) Assignee: Toyota Motor Engineering & Manufacturing North America, Inc., Plano, TX (US)

( * ) Notice: Subject to any disclaimer, the term of this patent is extended or adjusted under 35 U.S.C. 154(b) by 163 days.

(21) Appl. No.: 18/809,846

(22) Filed: Aug. 20, 2024

(65) Prior Publication Data

US 2026/0090783 A1 Apr. 2, 2026

(51) Int. Cl.
　　*A61B 7/00* (2006.01)
　　*A61B 7/04* (2006.01)
(52) U.S. Cl.
　　CPC ........ *A61B 7/04* (2013.01); *A61B 2560/0462* (2013.01); *A61B 2562/0204* (2013.01); *A61B 2562/14* (2013.01); *A61B 2562/168* (2013.01)
(58) Field of Classification Search
　　CPC .............. A61B 7/04; A61B 2560/0462; A61B 2562/0204; A61B 2562/14; A61B 2562/168
　　See application file for complete search history.

(56) References Cited

U.S. PATENT DOCUMENTS

| | | | |
|---|---|---|---|
| 10,786,162 B2 * | 9/2020 | Benson ................. | A61B 5/329 |
| 12,337,738 B2 * | 6/2025 | Abdella ................ | B60N 2/646 |
| 2018/0224937 A1 * | 8/2018 | Majkowski ............ | B60K 35/25 |
| 2020/0129237 A1 * | 4/2020 | Ay ......................... | G06T 19/20 |

FOREIGN PATENT DOCUMENTS

| | | | | |
|---|---|---|---|---|
| DE | 102018103396 A1 | 8/2019 | | |
| JP | 2022510389 A * | 1/2022 | ....... | B60R 21/01508 |
| KR | 20200039135 A * | 4/2020 | ............ | B60N 2/002 |
| KR | 1020200039135 A | 4/2020 | | |

* cited by examiner

*Primary Examiner* — Joel Lamprecht
(74) *Attorney, Agent, or Firm* — Dinsmore & Shohl LLP

(57) ABSTRACT

Embodiments herein are directed to a vehicle seat that has a rear surface and an occupant contact surface spaced apart from the rear surface to define a cavity therebetween is provided. The vehicle seat includes a sensor positioned within the cavity, at least one fluid medium positioned within the cavity and extending to the occupant contact surface, and at least one deflector member positioned within the cavity. The at least one deflector member is shaped and sized to at least partially surround the at least one fluid medium such that the at least one deflector member is configured to constrain and direct a plurality of heart sound waves through the at least one fluid medium to the sensor when an occupant is in contact with the occupant contact surface.

10 Claims, 15 Drawing Sheets

HEART RATE DETECTION ASSEMBLY AND METHODS OF DETECTING A HEART RATE

TECHNICAL FIELD

The present specification generally relates to heart rate detection devices, and more specifically, heart rate detection devices and methods of detecting a heart rate of an occupant within a seat of a vehicle.

BACKGROUND

Heart rate monitoring is commonly used to track an individual's health and well-being, particularly in individuals with pre-existing conditions. The health and well-being of an individual may be especially significant in high-risk situations, such as when the individual is operating a vehicle. Conventional heart rate monitor assemblies may monitor heart rate activity by mounting acoustic or vibration sensors on a vehicle seat. When the back of a user is in touch with the seat, the heart activity can be recorded. This technology is useful, but is vulnerable to noise—whenever the user moves, the friction generates substantial noise in the data, which may render the collection of heart data impossible. Additionally, the quality of the data depends on the position of the user's heart relative to the sensor. Therefore, anatomical differences of the user (height, body composition, and the like) may compromise the data quality. Moreover, the signal-to-noise ratio is extremely unfavorable, leading to measurement difficulties.

SUMMARY

In one embodiment, a vehicle seat that has a rear surface and an occupant contact surface spaced apart from the rear surface to define a cavity therebetween is provided. The vehicle seat includes a sensor positioned within the cavity, at least one fluid medium positioned within the cavity and extending to the occupant contact surface, and at least one deflector member positioned within the cavity. The at least one deflector member is shaped and sized to at least partially surround the at least one fluid medium such that the at least one deflector member is configured to constrain and direct a plurality of heart sound waves through the at least one fluid medium to the sensor when an occupant is in contact with the occupant contact surface.

In another embodiment, a system to identify a signal-to-noise ratio of a plurality of heart sound waves within a vehicle seat is provided. The system includes a sensor positioned within a cavity of the vehicle seat, at least one fluid medium positioned within the cavity, at least one deflector member positioned within the cavity, at least one actuation device positioned within the cavity, a processor communicatively coupled to the at least one actuation device, and a non-transitory, processor-readable storage medium in communication with the processor. The at least one deflector member is at least partially surrounding the at least one fluid medium such that the at least one deflector member is configured to constrain and direct the plurality of heart sound waves through the at least one fluid medium to the sensor when an occupant is positioned within the vehicle seat. The at least one deflector member is configured to selectively deform to channel the plurality of heart sound waves to the sensor. The non-transitory, processor-readable storage medium comprising one or more programming instructions that, when executed, cause the processor to obtain the signal-to-noise ratio of the plurality of heart sound waves, determine that the signal-to-noise ratio is not at a predetermined threshold, and in response, actuate the at least one actuation device to deform the at least one deflector member.

In yet another embodiment, a method for improving a signal-to-noise ratio of a plurality of heart sound waves from an occupant within a seat of a vehicle is provided. The method includes obtaining the signal-to-noise ratio of the plurality of heart sound waves, the plurality of heart sound waves obtained via a sensor positioned within at least one fluid medium positioned within a cavity of the seat, determining that the signal-to-noise ratio is not at a predetermined threshold, and in response, actuating at least one actuation device that is configured to deform at least one deflector member, the at least one deflector member positioned within the cavity, the at least one deflector member at least partially surrounding the at least one fluid medium such that the at least one deflector member is configured to constrain and direct the plurality of heart sound waves through the at least one fluid medium to the sensor.

These and additional features provided by the embodiments described herein will be more fully understood in view of the following detailed description, in conjunction with the drawings.

BRIEF DESCRIPTION OF THE DRAWINGS

The embodiments set forth in the drawings are illustrative and exemplary in nature and not intended to limit the subject matter defined by the claims. The following detailed description of the illustrative embodiments can be understood when read in conjunction with the following drawings, where like structure is indicated with like reference numerals and in which:

DETAILED DESCRIPTION

Figure 1A:
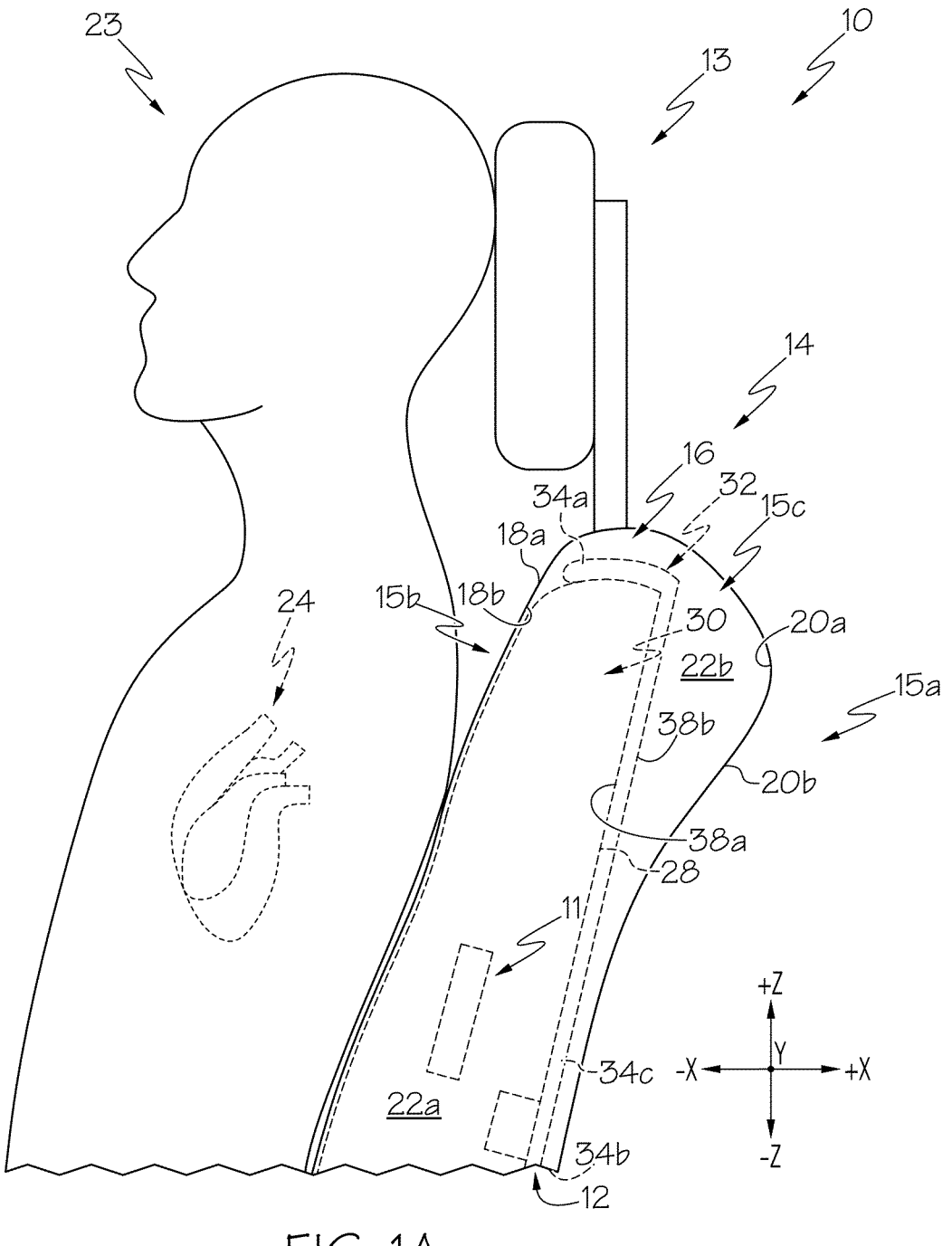
FIG. 1A schematically depicts a side view of an occupant and a seat that includes a heart rate monitoring device positioned within a vehicle, according to one or more embodiments shown and described herein.

Embodiments described herein are generally directed to heart rate detection assemblies and methods of detecting a heart rate of an occupant of a seat within a vehicle. As described herein, a vehicle seat may include a rear surface and an opposite occupant contact surface that is spaced apart from the rear surface to define a cavity therebetween. A sensor configured to detect a plurality of heart sound waves emitted from a heart of the user is positioned within the cavity. Additionally, at least one fluid medium is positioned within the cavity and extends to the occupant contact surface of the seat. The sensor is movably positioned within the at least one fluid medium. At least one deflector is positioned within the cavity and is shaped and sized to at least partially surround the at least one fluid medium such that the at least one deflector is configured to constrain and direct the plurality of heart sound waves through the at least one fluid medium to the sensor when a user is in contact with the occupant contact surface.

The at least one fluid medium has a similar acoustic impedance to the human body permitting the plurality of heart sound waves to travel through the at least one fluid medium to the sensor. The deflector has a different acoustic impedance value that is configured to reflect sound. Further, the deflector is configured to deform. As such, based on a manipulation of the deflector, the plurality of heart sound waves may be directed through the at least one fluid medium to minimize the noise and optimize the plurality of heart sound waves received and detected by the sensor. The sensor may be a microphone positioned within the cavity that detects, senses, records, or otherwise transmits data related to the plurality of heart sound waves. Further, the sensor may be movably positioned within the cavity of the seat such that based on a size or shape of the user in contact with the occupant contact surface, the sensor may move within the at least one fluid medium in response to the change or manipulation of the occupant contact surface.

The heart rate detection device described herein may provide a convenient and effective way to monitor heart health of the vehicle occupant while driving or riding in the vehicle. The device may also improve a user-seat interface compared to conventional systems and thus generating data collection with higher signal-to-noise ratio (SNR).

Various embodiments of the heart rate detection devices and methods of detecting a heart rate of a vehicle occupant will now be described herein. Whenever possible, the same reference numerals will be used throughout the drawings to refer to the same or like parts.

As used herein, the term "communicatively coupled" means that coupled components are capable of exchanging data signals and/or electric signals with one another such as, for example, electrical signals via conductive medium, electromagnetic signals via air, optical signals via optical waveguides electrical energy via conductive medium or a non-conductive medium, data signals wirelessly and/or via conductive medium or a non-conductive medium and the like. It should be understood that other means of connecting the various components of the system not specifically described herein are included without departing from the scope of the present disclosure.

As used herein, the term "longitudinal direction" refers to the forward-rearward direction of the seat (i.e., in the +/−seat X-direction depicted in FIG. 1A). The term "lateral direction" refers to the cross-vehicle direction (i.e., in the +/−seat Y-direction depicted in FIG. 1A), and is transverse to the longitudinal direction. The term "vertical direction" or "up" or "above" and "below" refer to the upward-downward direction of the seat (i.e., in the +/−seat Z-direction depicted in FIG. 1A).

Figure 1B:
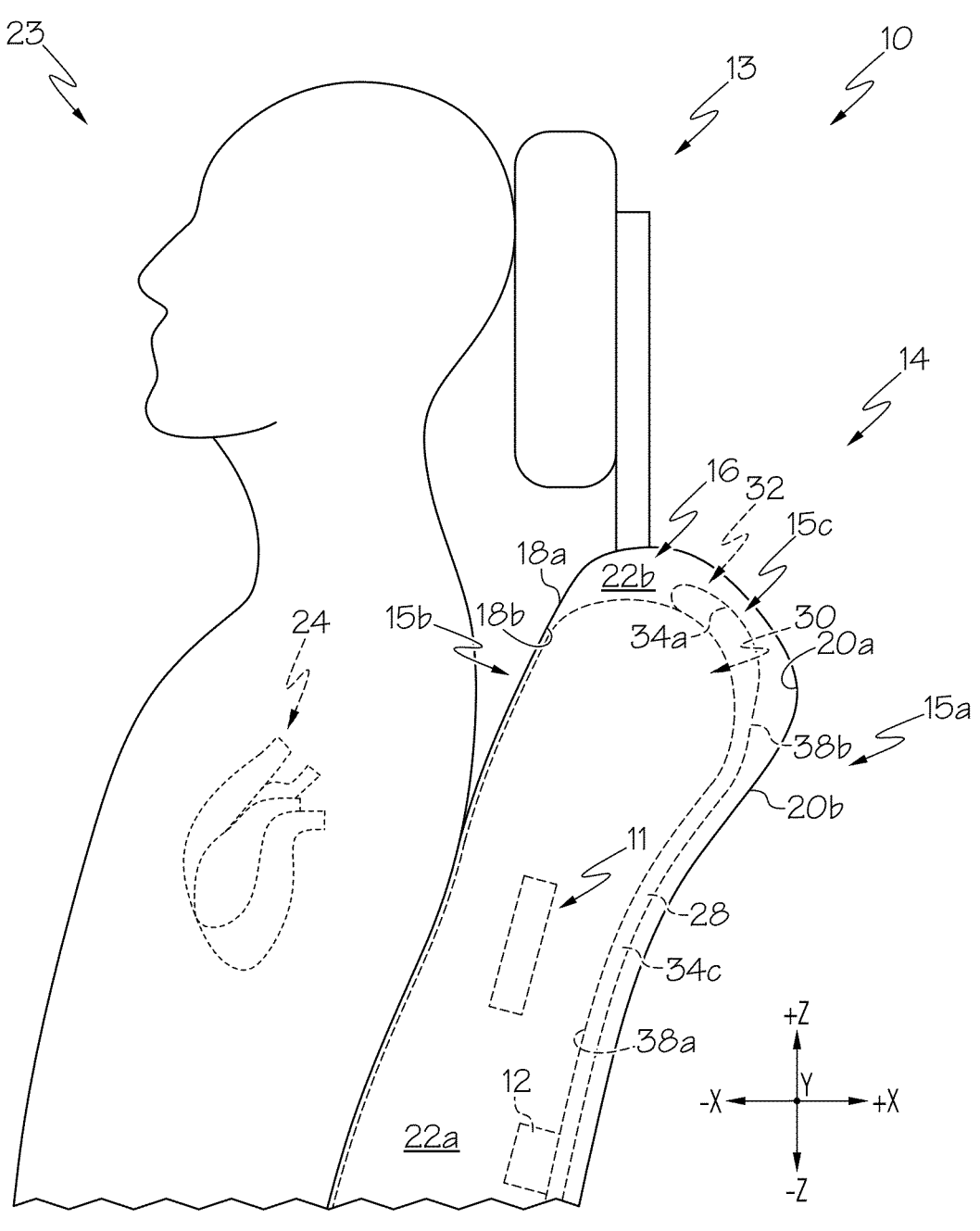
FIG. 1B schematically depicts the side view of the occupant and the seat of FIG. 1A with the occupant positioned against an occupant contact surface of a seatback of the seat, according to one or more embodiments shown and described herein.
Figure 1C:
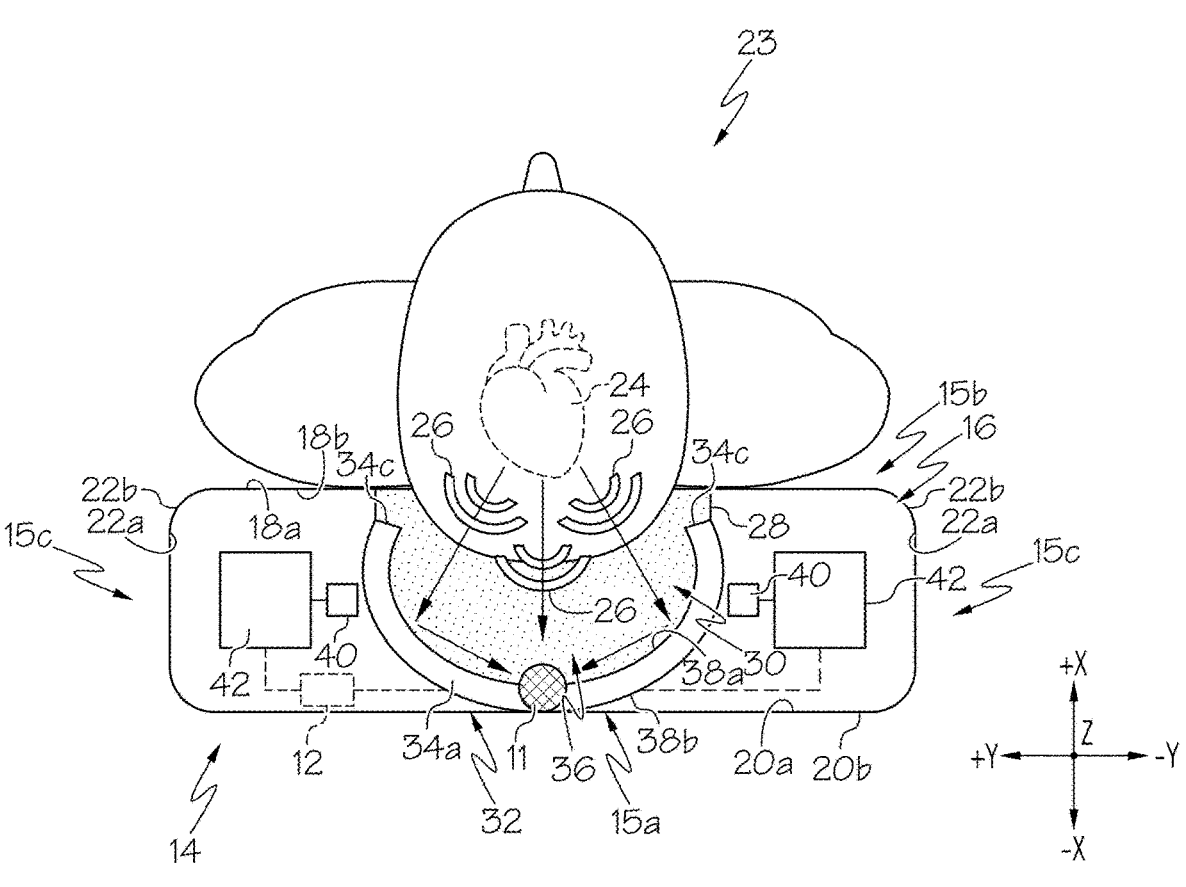
FIG. 1C schematically depicts a top-down view of the occupant and the seat of FIG. 1B, according to one or more embodiments shown and described herein.

Referring initially to FIGS. 1A-1C, a heart rate detection assembly 10 is depicted within a vehicle. In these embodiments, the heart rate detection assembly 10 may include a sensor 11 and an electronic control unit 12. Portions of the heart rate detection assembly 10 may be positioned and/or embedded within a seatback 14 of a seat 13 positioned within the vehicle, such that the heart rate detection assembly 10 may monitor or measure the heart rate of an occupant 23 that has engaged (e.g., sits) in the seat 13 without contact with the occupant 23 (e.g., contactless), as discussed in greater detail herein. Throughout the disclosure, contactless monitor or measure refers to monitoring and/or measuring a heart rate of the occupant 23 without direct physical contact. For example, contactless monitoring and/or measuring is found when the sensor 11 is embedded in the seatback 14 that is in contact with the clothing of the occupant 23 when the occupant 23 sits within the seat 13, as discussed in greater detail herein.

The sensor 11 may be movably positioned and/or movably embedded within a cavity 16 of the seatback 14 defined by a rear portion 15*a* and an opposite occupant contact portion 15*b* and a pair of side portions 15*c*. The occupant contact portion 15*b* includes an occupant contact surface 18*a* and an opposite inner surface 18*b*. The rear portion 15*a* includes a rear interior surface 20*a* and an opposite rear exterior surface 20*b*. Each of the pair of side portions 15*c* include a side exterior surface 22a and an opposite side interior surface 22b. The cavity 16 is defined by or positioned between the inner surface 18b, the rear interior surface 20a and both of the side interior surfaces 22b.

The sensor 11 may be positioned in the cavity 16 and is configured to detect, receive, record, and/or transmit a plurality of heart sound waves 26 emitted from a heart 24 of the occupant 23 in contact with the occupant contact portion 15b of the seat 13 to the electronic control unit 12, as best illustrated in FIG. 1C. In some embodiments, the sensor 11 may detect vibration through matter, such as air, liquid, and solids, that are influenced or otherwise modified by the plurality of heart sound waves 26 emitted by the heart 24 of the occupant 23.

As will be described in additional detail herein, the plurality of heart sound waves 26 emitted or generated by the heart 24 may be very faint, which may result in unfavorable signal-to-noise ratios and difficulties measuring the heart rate. Accordingly, by movably positioning the sensor 11 near the chest of the occupant 23 when the occupant 23 is positioned within the seat 13, and/or directing the plurality of heart sound waves 26 to the sensor 11, the heart rate detection assembly 10 may more easily obtain improved quality of heart rate measurements. As such, the sensor 11 is configured to be movable within the cavity 16 to meet specific anatomy differences between various occupants, as discussed in greater detail herein. That is, the sensor 11 may be movably positioned within the cavity 16 of the seatback 14 such that based on a size or shape of the occupant 23 in contact with the occupant contact surface 18a, the sensor 11 may move within the at least one fluid medium 30 in response to the change or manipulation of the occupant contact surface 18a, as discussed in greater detail herein.

For example, as best illustrated in FIG. 1A, the sensor 11 is positioned below the heart 24 of the occupant 23 in the vertical direction (e.g., in the +/−Z direction). Such an arrangement may occur when the occupant is not positioned to apply any or much force against the occupant contact surface 18a of the seatback 14. When the user is seated into the seat 13 and is positioned to apply a force against the occupant contact surface 18a of the seatback 14, the sensor 11 moves in the vertical direction (e.g., in the +/−Z direction) to be in an improved alignment with the heart 24 of the occupant 23, as best illustrated in FIG. 1B. As such, the sensor 11 is configured to be movably positioned within the cavity 16 of the seatback 14 such that the occupant contact surface 18a of the seatback 14 adjusts based on a size or shape of the occupant 23, and, in response, the sensor 11 may move within the at least one fluid medium 30 to better align the sensor 11 to the heart 24 of the occupant 23.

In some embodiments, the sensor 11 may be configured as an audio sensor, such as a microphone, configured to detect, sense, record, or otherwise transmit data related to the plurality of heart sound waves 26 to the electronic control unit 12. For example, the sensor 11 may be an air-coupled audio sensor, a condenser microphone, an electret microphone, a hydrophone, a piezoelectric microphone, and/or the like. The air-coupled audio sensor may use changes in air pressure to capture sound waves. The condenser microphone (or a capacitor microphone) may use a diaphragm and a back plate separated by a small air gap to capture sound. As such, the audio sensor may refer to a device that detects sound waves and converts the sound waves into electrical signals in a surrounding area. The sensor 11 may be communicatively coupled to the electronic control unit 12.

In other embodiments, the sensor 11 may be a vibration sensor configured to detect mechanical vibrations of matter, including air, liquid, and solids, and generate audio input signals to transmit to the electronic control unit 12. In these embodiments, the vibration sensor may be the microphone discussed above, a separate sensor, or a combination thereof. As such, in this embodiment, the sensor 11 may be configured to detect mechanical vibrations through the at least one fluid medium 30 caused by the plurality of heart sound waves 26 traveling there through.

In other embodiments, the sensor 11 may be an accelerometer sensor configured to detect, collect, and/or transmit velocity and displacement information as a function of time. In these embodiments, the accelerometer sensor may be in combination with either of the vibration sensor or the audio sensor, both the vibration sensor and the audio sensor, or may be a stand-alone sensor. In these embodiments, the accelerometer sensor may be configured to collect the vibrations generated by the plurality of heart sound waves 26 through the at least one fluid medium 30 generated by the occupant 23.

In some embodiments, the sensor 11 may have the capability to gather omnidirectional sounds, capturing sound equally from all directions without a specific emphasis on any particular source or direction. In other embodiments, the sensor 11 may gather sounds from specific directions to mitigate background noise. The choice between the omnidirectional and selective direction approaches may depend on the positioning of the at least one deflector member 32, the position of sensor 11, and/or the like, as discussed in greater detail herein. For example, the omnidirectional approach may be employed before or with minimal deformation of the at least one deflector member 32. On the other hand, the selective direction approach may be employed when the at least one deflector member 32 is deformed to direct the plurality of heart sound waves 26 to the sensor 11, as discussed in greater detail herein. Such an arrangement and deformation of the at least one deflector member 32 is to optimize the collection of the acoustics, vibrations, and the like, traveling through the at least one fluid medium 30 and to customize and/or tailor the collection of the acoustics, vibrations, and the like, traveling through the at least one fluid medium 30 based on the anatomy of the occupant 23 positioned within the seat 13.

Although the sensor 11 and the electronic control unit 12 of the heart rate detection assembly 10 are depicted as being integrated into the seatback 14 of the vehicle, it should be understood that the sensor 11 and/or the electronic control unit 12 may each independently, or together, be integrated into any component of the vehicle that allows the sensor 11 to detect the plurality of heart sound waves 26 of the occupant 23 in the manner described above with respect to the various embodiments of the sensor 11 and/or the electronic control unit 12 to receive data from the sensor 11 with respect to the plurality of heart sound waves 26 of the occupant 23 positioned within the seat 13. For example, the sensor 11 and/or the electronic control unit 12 may similarly be embedded in a seat cushion of the seat 13 of the vehicle.

Still referring to FIGS. 1A-1C, in some embodiments, a bladder 28 may be positioned within the cavity 16 of the seatback 14. The bladder 28 may be pliable such that the bladder 28 may be easily deformed with minimal influence, such as by the occupant 23 making contact with the occupant contact surface 18a of the seatback 14. Matter may be filled within the bladder 28. For example, at least one fluid medium 30 is positioned within the bladder and configured to allow the sensor 11 to move within the at least one fluid medium 30 based on an amount of pressure or force applied to the specific portions of the occupant contact surface 18a of the seatback 14 by the occupant 23. That is, because the bladder 28 and the at least one fluid medium 30 are positioned to be within the cavity 16 to abut or contact portions of the inner surface 18b of the seatback 14, when the occupant 23 sits in the seat 13 and applies a pressure or force against the occupant contact surface 18a, in response, the bladder 28 and/or the at least one fluid medium 30 are manipulated to conform to the anatomy of the occupant 23, thus moving the sensor 11 within the cavity 16 into a position that is better aligned with the heart 24 of the occupant 23, as best illustrated in FIG. 1B. It should be appreciated that in other embodiments, the bladder 28 may include solids, multiple types of fluids (e.g., air, liquids, and the like), combinations thereof, and the like. As such, the at least one fluid medium 30 is not limited to a single fluid or matter and may be a plurality of fluids and/or matters including a plurality of different liquids, solids and gasses.

In other embodiments, portions of the cavity 16, surfaces of the seatback 14 (e.g., the occupant contact surface 18a), and at least one deflector member 32 may be configured to retain the at least one fluid medium 30, thus acting as the bladder 28. As such, the bladder 28 is not needed. That is, in these embodiments, the at least one fluid medium 30 is positioned within the cavity 16 and still configured to allow the sensor 11 to move within the at least one fluid medium 30 based on an amount of pressure applied to the occupant contact surface 18a of the seatback 14 by the occupant 23, but various seatback components or structures act as the bladder to retain the at least one fluid medium 30 into various positions based on the amount of pressure or force applied to the occupant contact surface 18a.

Still referring to FIGS. 1A-1C, in some embodiments, the at least one deflector member 32 is positioned within the cavity 16 and is spaced apart from the occupant contact surface 18a. The at least one deflector member 32 is shaped and sized to at least partially surround the at least one fluid medium 30 (and bladder 28, if included) such that the at least one deflector member 32 is configured to constrain at least a portion of the at least one fluid medium 30 (and bladder 28, if included). The at least one deflector member 32 is positioned to not interfere with the occupant contact surface 18a of the seatback 14 such that the at least one fluid medium 30 (and bladder 28, if included) may be manipulated by the anatomy of the occupant 23, as discussed in greater detail herein. The at least one deflector member 32 is positioned to be selectively deformed to further manipulate the at least one fluid medium 30 (and bladder 28, if included) to further move the sensor 11 within the at least one fluid medium 30 to optimize the gathering of the plurality of heart sound waves 26 emitted or generated by the heart 24 of the occupant 23, as discussed in greater detail herein. That is, the at least one deflector member 32 is configured to be selectively deformable, which in turn further manipulates the at least one fluid medium 30 while simultaneously creating a device that directs the plurality of heart sound waves 26 through the at least one fluid medium 30 in an optimized direction to the sensor 11, reducing the signal-to-noise ratio at the sensor 11, improving the detection of the plurality of heart sound waves 26.

It should be appreciated that the at least one fluid medium 30 has a similar acoustic impedance to the human body permitting the plurality of heart sound waves 26 to travel through the at least one fluid medium 30 to the sensor 11 similar to how the sound waves travel through the human body. On the other hand, the at least one deflector member 32 has a different acoustic impedance value that is configured to reflect sound. Further, because the at least one deflector member 32 is configured to deform, based on the deformation or manipulation of the at least one deflector member 32, the plurality of heart sound waves 26 may be directed through the at least one fluid medium 30 to minimize the noise and optimize the plurality of heart sound waves 26 received and/or detected by the sensor 11. That is, the at least one deflector member 32 may be used to further change or manipulate the at least one fluid medium 30 to move the sensor 11 into an optimal position or location within the cavity 16, while also, or simultaneously deforming to form an acoustic deflector to direct the plurality of heart sound waves 26 to the sensor 11.

Example fluids of the at least one fluid medium 30 may include, without limitation, water, air, propylene glycerine, glycol, propanediol, dipropylene glycol, butylene glycol, combinations thereof, and/or the like. Examples of the at least one deflector member 32 materials include, without limitation, polymers, glass, silicone, ceramics, nylon, Teflon, epoxy, polyethylene, polyester, combinations thereof, and/or the like. As such, the at least one deflector member 32 may be a resilient member that is deformable or semi-rigid to act as a wall to direct sound, vibrations, and the like, to the sensor 11. As such, it should be understood that the material characteristics of the at least one deflector member 32 has an acoustic impedance that reflects sounds while the at least one fluid medium 30 is similar to the human body and has an acoustic impedance that is transparent. As such, the at least one deflector member 32 and the at least one fluid medium 30 have different acoustic impedances.

In some embodiments, the at least one deflector member 32 may be a single monolithic structure. In some embodiments, the at least one deflector member 32 is conical shaped and sized to at least partially surround the at least one fluid medium 30 such that the at least one deflector member 32 is configured to constrain and direct the plurality of heart sound waves 26 through the at least one fluid medium 30 to the sensor 11 when the occupant 23 is in contact with the occupant contact surface 18a. In this embodiment, the at least one deflector member 32 includes an upper terminating surface 34a, an opposite lower terminating surface 34b, and a pair of side terminating surfaces 34c that define an opening 36 along an inner surface 38a in which the at least one fluid medium 30 may be positioned within to extend and abut the occupant contact surface 18a of the seatback 14. Further, the at least one deflector member 32 includes an opposite outer surface 38b spaced apart from the inner surface 38a to define a thickness of the at least one deflector member 32. In this embodiment, the opening 36 at the upper terminating surface 34a may have a smaller diameter or circumference than the opening 36 at the lower terminating surface 34b, which is positioned closer to the cushion of the seat 13, such that the at least one deflector member 32 tapers in the vertical direction (e.g., in the +/−Z direction). The at least one fluid medium 30 may be configured to be manipulated within the opening 36 of the at least one deflector member 32 by pressure or force applied to the occupant contact surface 18a of the seatback 14 caused by the occupant 23 sitting in the seat 13, thereby changing the shape of the occupant contact surface 18a of the seatback 14, which in response, changes the shape of the at least one fluid medium 30 and the at least one deflector member 32, as best illustrated in FIG. 1B.

In other embodiments, the at least one deflector member 32 is generally C-shaped and sized to at least partially surround the at least one fluid medium 30 such that the at least one deflector member 32 is configured to partially constrain the at least one fluid medium 30 and direct the plurality of heart sound waves 26 through the at least one fluid medium 30 to the sensor 11 when the occupant 23 is in contact with the occupant contact surface 18a, as best illustrated in FIGS. 1B-1C. That is, the general C-shape of the at least one deflector member 32 still includes the upper terminating surface 34a, the opposite lower terminating surface 34b, and the pair of side terminating surfaces 34c that define the opening 36 in which the at least one fluid medium 30 may be positioned within to extend and abut the occupant contact surface 18a of the seatback 14. In this embodiment, the opening 36 at the upper terminating surface 34a may have a uniform diameter or circumference such that the opening 36 remains uniform in the vertical direction (e.g., in the +/−Z direction) between the upper terminating surface 34a and the lower terminating surface 34b. The at least one fluid medium 30 may be configured to be manipulated within the opening 36 of the C-shape via pressure or force applied to the occupant contact surface 18a of the seatback 14 caused by the occupant 23 sitting in the seat 13. That is, the at least one fluid medium 30 may be configured to be manipulated within the opening 36 of the at least one deflector member 32 via the position of and/or the amount of pressure or force applied to the occupant contact surface 18a of the seatback 14 caused by the occupant 23. As such, the position of and/or the amount of pressure or force applied changes the shape of the occupant contact surface 18a, which in turn changes the shape of the at least one fluid medium 30 and may change the shape of the at least one deflector member 32.

In other embodiments, the at least one deflector member 32 may be any shape or size, may be irregular in shape or uniform in shape, the opening 36 may be tapered, uniform, and/or irregular, and the like.

Further, the at least one deflector member 32 may be deformed, to further manipulate the at least one fluid medium 30 to optimize the collection of the acoustics and/or vibrations traveling through the at least one fluid medium 30, as discussed in greater detail herein. In other embodiments, the at least one deflector member 32 may be two or more separate or independent pieces or members that are movably coupled to one another and are configured to deform together as a single member or may be configured to deform independently with respect to one another. In this embodiment, each of the members may include a bore, or half circle that when coupled together form a bore that allows for the sensor 11 to be positioned therein.

Figure 6:
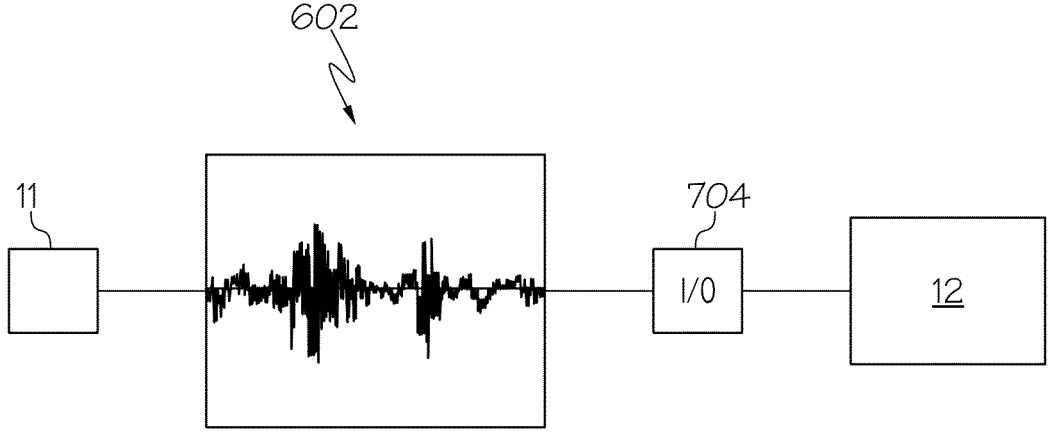
FIG. 6 schematically depicts an illustrative signal processing architecture for detecting and improving a signal-to-noise ratio of a plurality of heart sound waves emitted by the occupant positioned in the seat, according to one or more embodiments shown and described herein.

Now referring to FIG. 6, schematically depicted is an overview of the hardware and software components that may be utilized to determine and improve a signal-to-noise ratio. Collected signals 602 are detected, received, and/or gathered by the sensor 11 from the plurality of heart sound waves 26 (FIG. 1C) and may be transmitted to the electronic control unit 12 through input/output hardware 704 of the electronic control unit 12. The electronic control unit 12 is configured to identify a plurality of heart sound waves and a corresponding signal-to-noise ratio thereof by utilizing hardware, software, and/or firmware, according to embodiments shown and described herein.

Figure 7:
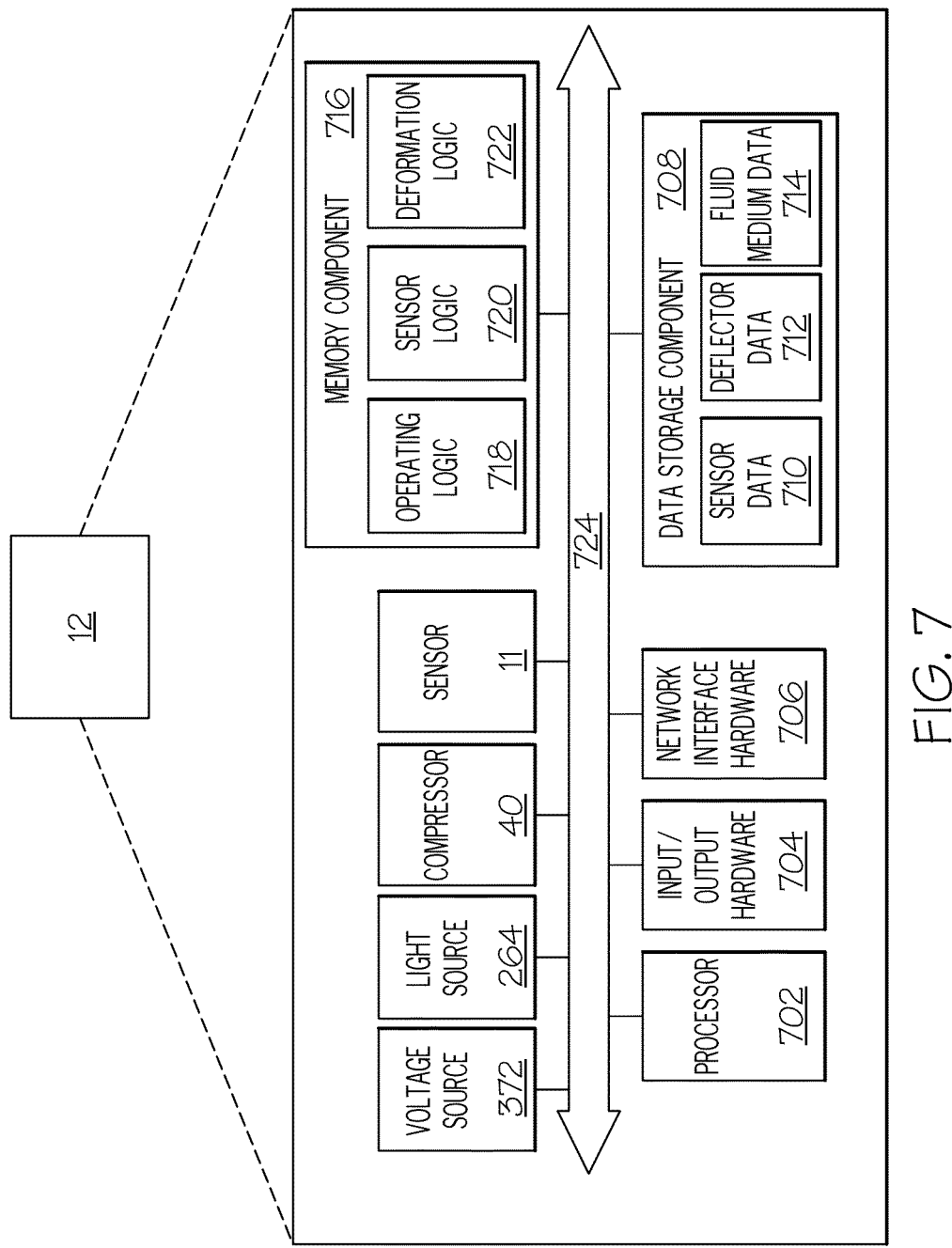
FIG. 7 schematically depicts an illustrative electronic control unit, further illustrating hardware and software components that may be used to detect and improve the signal-to-noise ratio of the plurality of heart sound waves emitted by the occupant positioned in the seat, according to one or more embodiments described and illustrated herein.

Now referring to FIG. 7, the electronic control unit 12 may include a non-transitory, computer readable medium configured for receiving data from external components, such as the collected signals 602 (FIG. 6) from the sensor 11, determining a signal-to-noise ratio of the data, and identifying whether the signal-to-noise ratio is of a quality necessary to determine a heart rate of the occupant 23 (FIG. 1C) embodied as hardware, software, and/or firmware, according to embodiments shown and described herein.

While in some embodiments, the electronic control unit 12 may be configured as a general-purpose computer with the requisite hardware, software, and/or firmware, in other embodiments, the electronic control unit 12 may be configured as a special purpose computer designed specifically for performing the functionality described herein. For example, the electronic control unit 12 may be a specialized device that particularly determines signal-to-noise ratios, extracts heart sounds from other audio and other noise, and further optimizes the sensing of the plurality of heart sound waves 26 via the collected signals 602 (FIG. 6) by further deforming or manipulating the at least one deflector member 32 (FIG. 1C), and increasing the signal-to-noise ratio, as discussed in greater detail herein. The electronic control unit 12 is configured for the purposes of improving the accuracy of gathered data by the sensor 11, improvement in recognizing heart sounds through the at least one fluid medium 30, and improving signal-to-noise ratio.

As also illustrated in FIG. 7, the electronic control unit 12 may include a processor 702, input/output hardware 704, network interface hardware 706, and a data storage component 708, which stores a database of sensor data 710, deflector data 712, and fluid medium data 714, and a memory component 716. The memory component 716 may be non-transitory computer readable memory. The memory component 716 may be configured as volatile and/or non-volatile memory and, as such, may include random access memory (including SRAM, DRAM, and/or other types of random access memory), flash memory, registers, compact discs (CD), digital versatile discs (DVD), and/or other types of storage components. Additionally, the memory component 716 may be configured to store operating logic 718, sensor logic 720, and deformation logic 722 (each of which may be embodied as a computer program, firmware, or hardware, as an example). A local interface 724 is also included in FIG. 7 and may be implemented as a bus or other interface to facilitate communication among the components of the electronic control unit 12.

The processor 702 may include any processing component(s) configured to receive and execute one or more programming instructions (such as from the data storage component 708 and/or memory component 716). Further, the processor 702 may be any device capable of executing the machine-readable instruction set stored in the non-transitory computer readable memory. The machine-readable instruction set may comprise logic or algorithm(s) written in any programming language of any generation (e.g., 1GL, 2GL, 3GL, 4GL, or 5GL) such as, for example, machine language that may be directly executed by the processor 704, or assembly language, object-oriented programming (OOP), scripting languages, microcode, etc., that may be compiled or assembled into machine-readable instructions and stored in the memory component 716. Alternatively, the machine-readable instruction set may be written in a hardware description language (HDL), such as logic implemented via either a field-programmable gate array (FPGA) configuration or an application-specific integrated circuit (ASIC), or their equivalents. Accordingly, the functionality described herein may be implemented in any conventional computer programming language, as pre-programmed hardware elements, or as a combination of hardware and software components. For example, the memory component 716 may be a machine-readable memory (which may also be referred to as a non-transitory processor-readable memory or medium) that stores instructions that, when executed by the processor 702, cause the processor 702 to perform a method or control scheme as described herein.

The input/output hardware 704 may include the capability to receive data from the sensor 11 and to provide an output from the electronic control unit 12. Example peripheral devices associated with the input/output hardware 704 may include, without limitations, a monitor, keyboard, mouse, printer, camera, microphone, speaker, and/or other devices for receiving, sending, and/or presenting data. The network interface hardware 706 may include any wired or wireless networking hardware, such as a modem, LAN port, wireless fidelity (Wi-Fi) card, WiMax card, mobile communications hardware, CAN BUS, and/or other hardware for communicating with other networks and/or devices, such as with other devices within the vehicle or external to the vehicle.

It should be understood that the data storage component 708 may reside local to and/or remote from the electronic control unit 12 and may be configured to store one or more pieces of data for access by the electronic control unit 12 and/or other components. As illustrated in FIG. 7, the data storage component 708 stores a database of sensor data 710, deflector data 712, and the fluid medium data 714. The sensor data 710 may store data related to the type of sensor (e.g., acoustic, vibration, acceleration, and/or the like), and data transmitted from the sensor 11. For example, the plurality of heart sound waves 26 (FIG. 1C) along with other noise sensed by the sensor 11, data related to signal-to-noise ratio, and the like. The deflector data 712 may store data related to the type of the at least one deflector member 32 (FIG. 1C) (e.g., material, quantity, and the like), the various devices used to deform the at least one acoustic deflector (e.g., compressor 40, the inflatable cushions 42 (FIG. 2A), the light source 264, the pneumatic honeycomb network 150 (FIG. 3B), the voltage source 372, the plurality of high voltage sheets 370 (FIG. 5A), and the like), current positioning of these various devices or states thereof used to deform the at least one acoustic deflector, and/or current positioning of the at least one deflector member 32 (FIG. 1C), and the like. The fluid medium data 714 may store data related to the type of the at least one fluid medium 30 (FIG. 1C) (e.g., material, quantity, and the like), positioning of the at least one fluid medium 30 (FIG. 1C) with respect to the at least one deflector member 32 (FIG. 1C), and positioning of the sensor 11 within the at least one fluid medium 30.

Included in the memory component 716 are the operating logic 718, sensor logic 720, and deformation logic 722. The operating logic 718 may include an operating system and/or other software for managing components of the electronic control unit 12. The sensor logic 720 may contain programming instructions to facilitate use of the sensor 11, activation of the sensor 11, analysis of the signal-to-noise ratio associated with the gathered data, analysis of the plurality of heart sound waves 26 (FIG. 1C) transmitted through the at least one fluid medium 30 (FIG. 1C), and the like. Further, the deformation logic 722 may contain programming instructions to instruct the various devices (e.g., compressor 40, the inflatable cushions 42 (FIG. 2A), the light source 264, the pneumatic honeycomb network 150 (FIG. 3B), the voltage source 372, the plurality of high voltage sheets 370 (FIG. 5A), and the like) configured to perform some electrical or mechanical movement, resulting in deforming of the at least one deflector member 32 (FIG. 1C) to further move or position the sensor 11, direct the plurality of heart sound waves 26 (FIG. 1C), and the like, which improves the quality of the data gathered by the sensor 11, increasing or improving the signal-to-noise ratio.

It should be understood that the components depicted in FIGS. 6-7 are merely illustrative and are not intended to limit the scope of this disclosure. More specifically, while the components in FIG. 7 are illustrated as residing within the electronic control unit 12, this is a nonlimiting example. In some embodiments, one or more of the components may reside external to the electronic control unit 12. Similarly, while FIG. 7 is directed to the electronic control unit 12, other components such as a user computing device, an administrator computing device, or other devices external to the electronic control unit 12 may include similar hardware, software, and/or firmware to be used in place of the electronic control unit 12 and/or in addition to the electronic control unit 12.

Figure 2A:
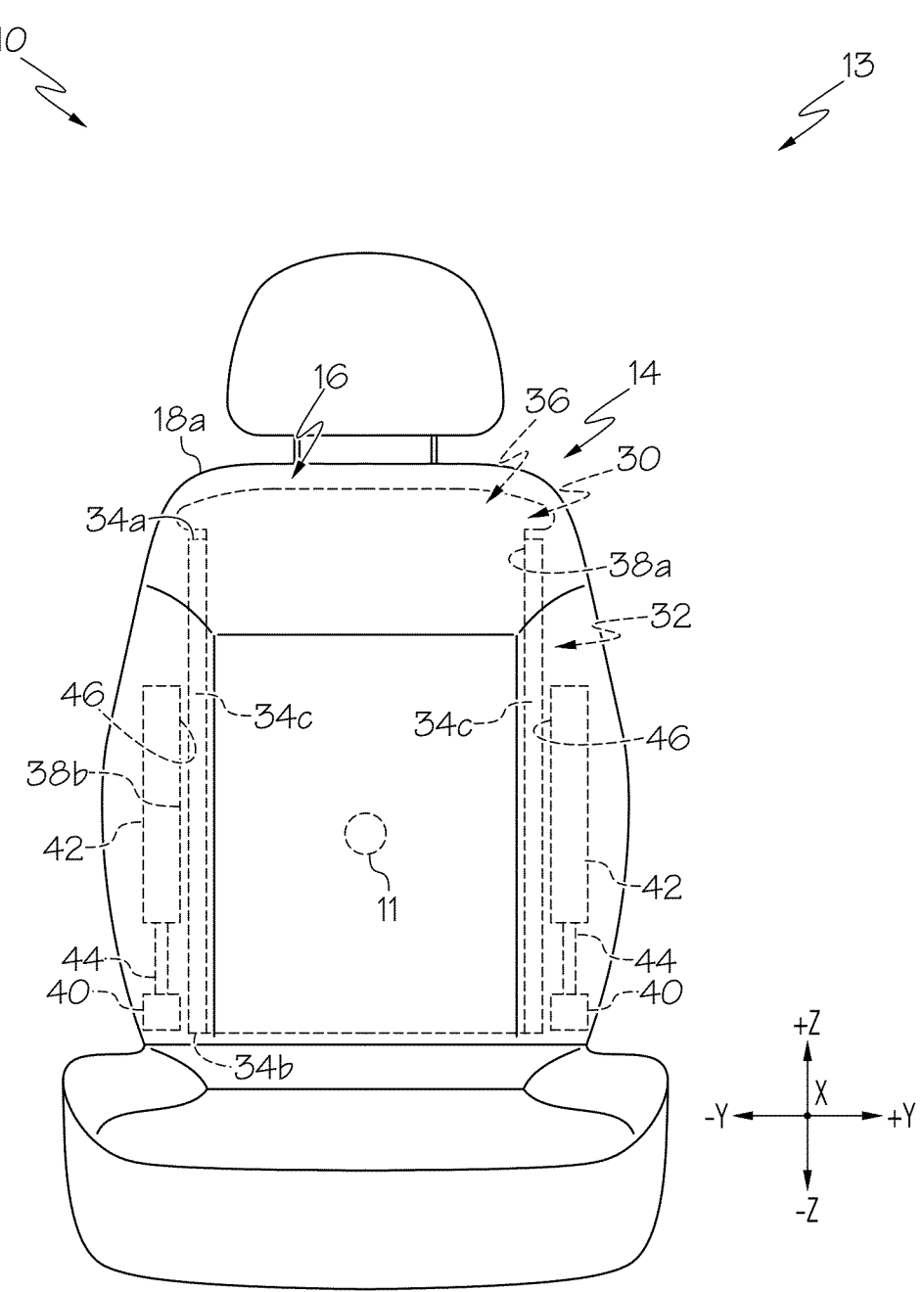
FIG. 2A schematically depicts a front plan view of a seat that includes a first aspect of a heart rate detection assembly depicted in a deflated state, according to one or more embodiments shown and described herein.
Figure 2B:
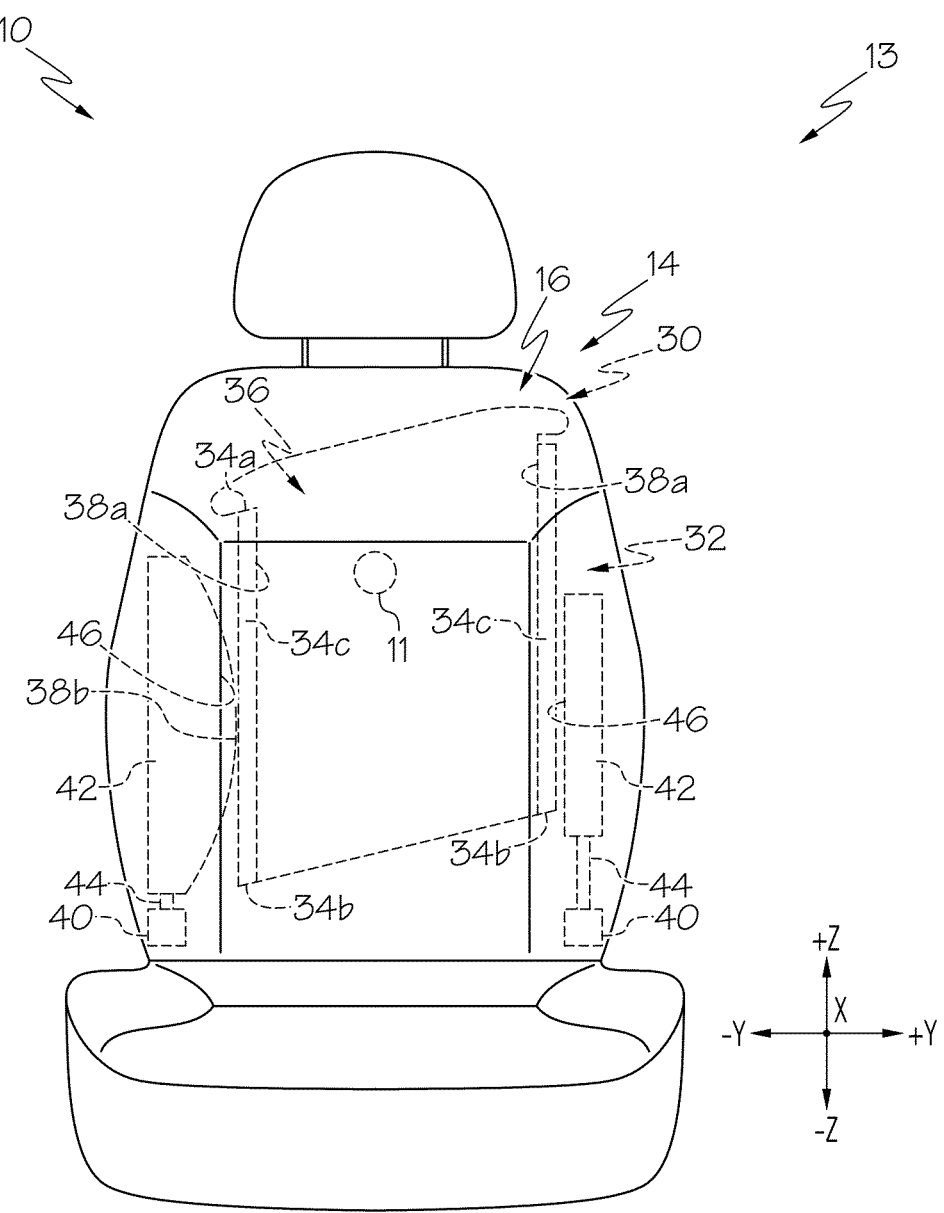
FIG. 2B schematically depicts the front plan view of the seat that includes the first aspect of the heart rate detection assembly of FIG. 2A depicted in a partially inflated state, according to one or more embodiments shown and described herein.

Now referring to back to FIG. 1C and to FIGS. 2A-2B, in the depicted embodiment, the cavity 16 of the seatback 14 further includes at least one actuation device, depicted as a pair of compressors 40 that are fluidly coupled to a pair of inflatable cushions 42 via at least one connection 44. It should be understood that the at least one actuation device is not limiting, and may be any actuator, motor, fluid driven, mechanically driven, and/or the like. In the depicted embodiment, each of the pair of inflatable cushions 42 are positioned within the cavity 16 and external to the opening 36 of the at least one deflector member 32. That is, each of the pair of inflatable cushions 42 are positioned and configured to make contact with at least the outer surface 38b of the at least one deflector member 32. It should be understood that each of the pair of inflatable cushions 42 may be an inflatable air pocket, an inflatable air envelope, or the like, that is configured to selectively inflate and retain a fluid, such as air or other gases. As such, upon inflation, each of the pair of inflatable cushions 42 may contact the outer surface 38b to further deform the at least one deflector member 32 by moving or manipulating at least one of the pair of side terminating surfaces 34c, and/or other parts or surfaces of the at least one deflector member 32, which in turn may manipulate, deform, or otherwise move the upper terminating surface 34a, the lower terminating surface 34b, other portions of the side terminating surfaces 34c, and/or the opening 36 of the at least one deflector member 32.

That is, each of the pair of inflatable cushions 42 are constrained by the cavity 16 of the seatback 14 such that upon inflation, an exterior surface 46 of at least one of the pair of inflatable cushions 42 contacts the outer surface 38b of the at least one deflector member 32 to deform to the at least one deflector member 32. The deformation of the at least one deflector member 32 further changes the shape of the at least one fluid medium 30 in a predetermined manner to move the sensor 11, as best depicted in FIG. 2B. In response, there is improved acoustic detection by the sensor 11, improvements in capturing the plurality of heart sound waves 26 by reducing noise, and the like. In the depicted embodiment, the sensor 11 is moved upon inflation of at least one inflatable cushion of the pair of inflatable cushions 42 in the vertical direction (e.g., in the +/−Z direction) to better position the sensor 11 with respect to the heart 24 of the occupant 23 and to better channel the acoustics in the at least one fluid medium 30 by the deformation of the at least one deflector member 32 to the sensor 11. This is nonlimiting, it should be understood that upon inflation of at least one inflatable cushion of the pair of inflatable cushions 42, the sensor 11 may be moved in any direction, including the longitudinal direction (e.g., in the +/−X direction), the lateral direction (e.g., in the +/−Y direction), the vertical direction (e.g., in the +/−Z direction), and/or combinations thereof, to better position the sensor 11 with respect to the heart 24 of the occupant 23.

Additionally, in the depicted embodiment, the pair of inflatable cushions 42 are depicted as positioned within the cavity 16 of the seatback 14 on either side of the at least one deflector member 32. This is non-limiting and either or both of the pair of inflatable cushions 42 may be positioned anywhere along the at least one deflector member 32 between the outer surface 38b of the at least one deflector member 32 and the inner surface 18b and/or the rear interior surface 20a of the seatback 14. Further, it should be understood that there may only be one inflatable cushion or more than two inflatable cushions. Further, the inflatable cushions may include segments or compartments that may inflate and/or deflate independently from one another.

It should also be understood that for illustrative purposes, one of the pair of inflatable cushions 42 is depicted as in a fully inflated state while the other one of the pair of inflatable cushions 42 is depicted in a deflated state, or not inflated. This is to simply illustrate for simplicity purposes that the inflation of the one of the pair of inflatable cushions 42 may deform the at least one deflector member 32 thereby deforming the at least one fluid medium 30. In response, the sensor 11 is further moved by the at least one fluid medium 30 to position the sensor 11 in an improved position to gather quality heart sounds from the occupant and the deformation of the at least one deflector member 32 may direct the sounds within the at least one fluid medium 30 to the sensor 11. As such, both the pair of inflatable cushions 42 may be inflated to equal inflation, one may be inflated more than the other, one may not be inflated at all, and the like, to deform the at least one deflector member 32 as desired.

In some embodiments, each of the pair of inflatable cushions 42 may be formed from a polyurethane nylon fabric. In other embodiments, each of the pair of inflatable cushions 42 may be formed from nylon, rubber, silicone, neoprene, and/or the like.

Further, in the depicted embodiment, the pair of compressors 40 are depicted as one for each of the pair of inflatable cushions 42. This is non-limiting and there may be one compressor or more than two compressors that are fluidly coupled to the pair of inflatable cushions 42. Further, in the depicted embodiment, the pair of compressors 40 are depicted as positioned within the cavity 16 of the seatback 14. This is non-limiting and each of the pair of compressors 40 may be positioned anywhere within the vehicle, such as with the seat cushion, floorboard, and the like.

Each of the pair of compressors 40 may be communicatively coupled to the electronic control unit 12 such that the electronic control unit 12 may control each one of the pair of compressors 40, and the inflation of each of the pair of inflatable cushions 42, which may be inflated to any degree of fill, including none at all to 100 percent capacity, necessary to change or manipulate the positioning of the at least one fluid medium 30 within the opening 36 of the at least one deflector member 32 and direct the plurality of heart sound waves 26 to the sensor 11 by the deformation of the at least one deflector member 32. As such, the electronic control unit 12 may monitor the signal-to-noise ratio and the quality of the plurality of heart sound waves 26 captured by and transmitted by the sensor 11 to adjust the positioning of the sensor 11 based on the varying anatomy of the occupant 23 positioned in the seat and/or directing of the plurality of heart sound waves 26 via positioning of the at least one deflector member 32.

Figure 3A:
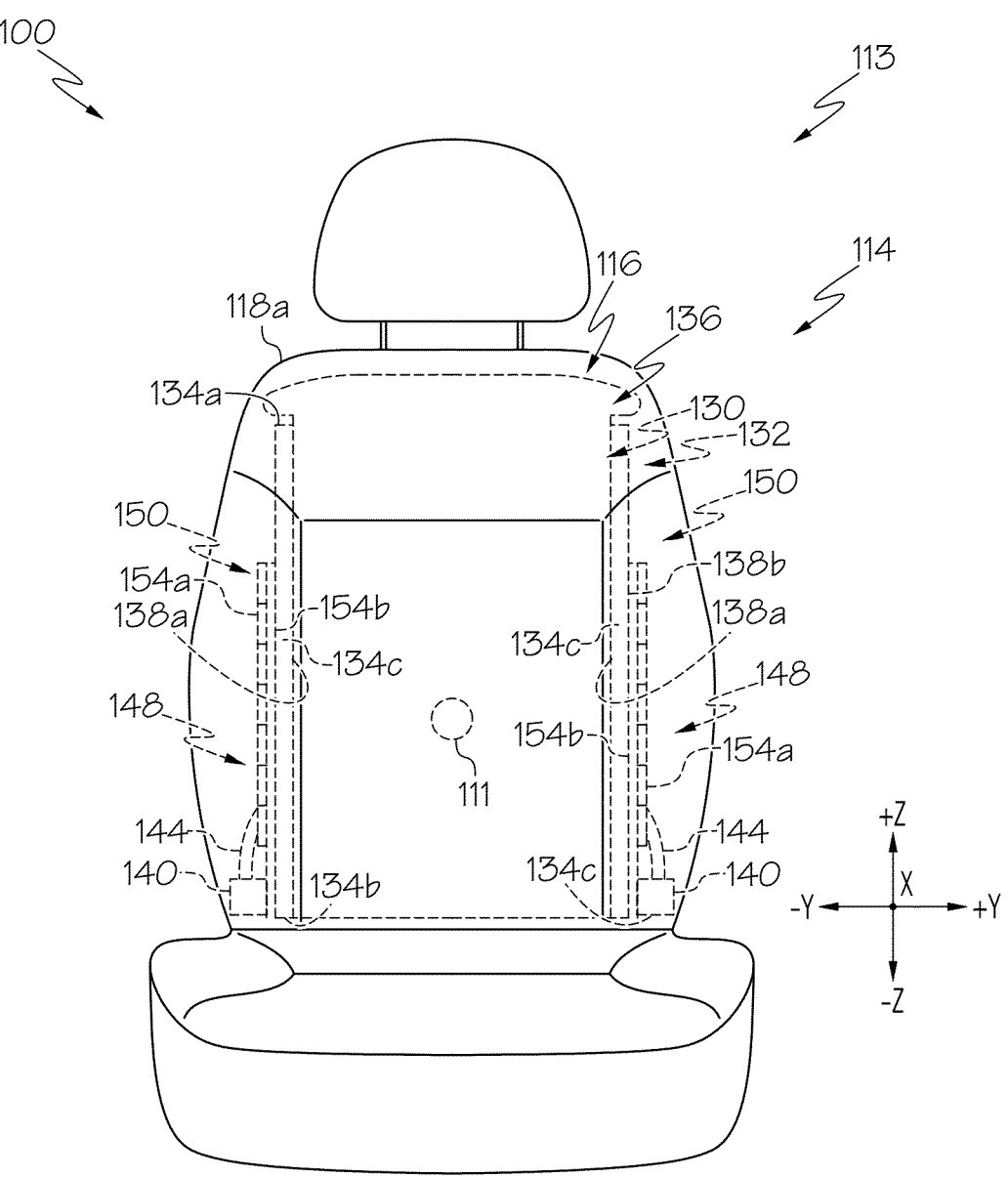
FIG. 3A schematically depicts a front plan view of a seat that includes a second aspect of a heart rate detection assembly depicted in an inactivated state, according to one or more embodiments shown and described herein.
Figure 3B:
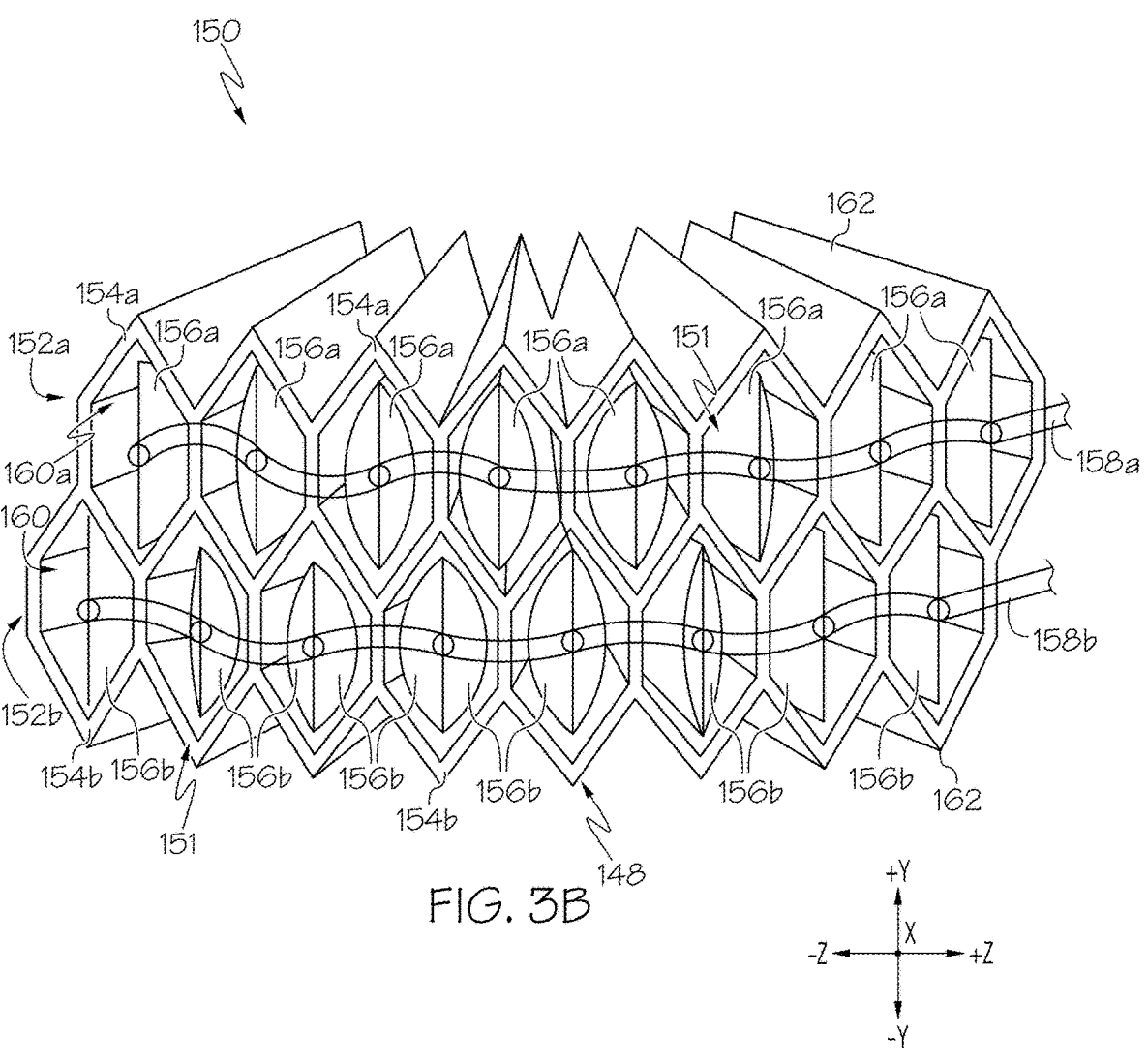
FIG. 3B schematically depicts a front perspective view of a pneumatic honeycomb network of the second aspect of the heart rate detection assembly of FIG. 3A, according to one or more embodiments shown and described herein.
Figure 3C:
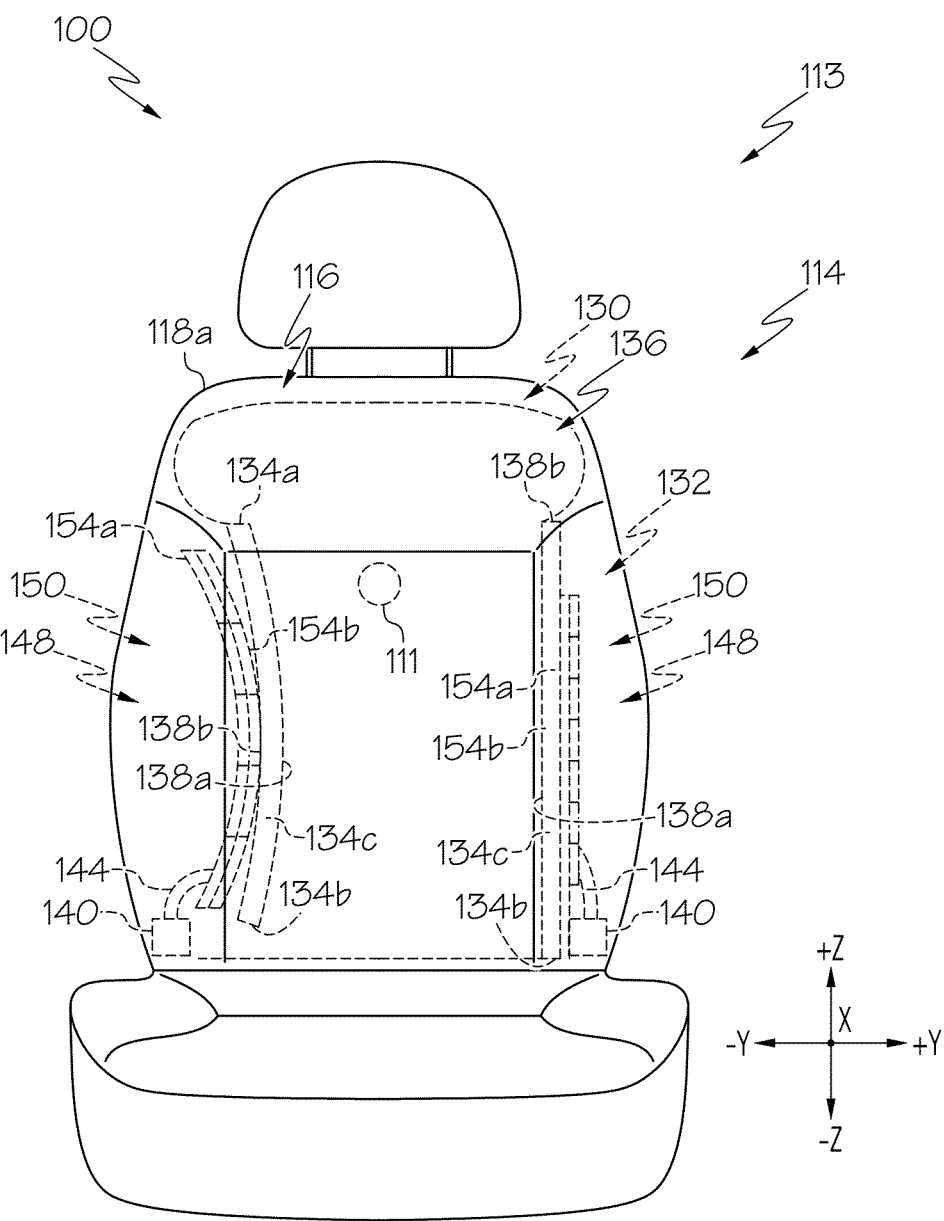
FIG. 3C schematically depicts the front plan view of the seat that includes the second aspect of the heart rate detection assembly of FIG. 3A depicted in a partially activated state, according to one or more embodiments shown and described herein.

Now referring to FIGS. 3A-3C, a second aspect of a heart rate detection assembly 100 is schematically depicted. It is understood that the heart rate detection assembly 100 is similar to the heart rate detection assembly 10 with the exceptions of the features described herein. As such, like features will use the same reference numerals with a prefix "1" for the reference numbers. For brevity reasons, these features will not be described again. Further, it should be understood that some or all reference characters are repeated in the description of FIGS. 3A-3C, but may not be specifically depicted in FIGS. 3A-3C.

In the depicted embodiment, the at least one actuation device is depicted as the pair of compressors 140 that are fluidly coupled to a plurality of inflatable cushions 148, which are positioned to define a pneumatic honeycomb network 150. The pneumatic honeycomb network 150 is configured as a device that generates robot moves through the folding-extension deformation of a plurality of hexagonal structures 151, causing structural deformation actuation by a soft arm member.

In the depicted embodiment, the pneumatic honeycomb network 150 includes two rows 152a, 152b of a plurality of honeycomb units 154a, 154b arranged in a vertical direction (e.g., in the +/−Z direction) above one another. Further, each of the two rows 152a, 152b of the plurality of honeycomb units 154a, 154b are staggered or offset in the longitudinal direction (e.g., in the +/−X direction) and/or in the lateral direction (e.g., in the +/−Y direction), and/or in the vertical direction (e.g., in the +/−Z direction). A first row plurality of inflatable cushions 156a are positioned to extend along the first row 152a such that the first row plurality of inflatable cushions 156a are generally positioned within a corresponding one of the plurality of honeycomb units 154a, which are formed in an accordion arrangement. A first plurality of tubes 158a or hoses are fluidly connected between each one of the first row plurality of inflatable cushions 156a and the corresponding honeycomb units 154 to manipulate or move the pneumatic honeycomb network 150, as discussed in greater detail herein. In some embodiments, the first plurality of tubes 158a may be fluidly connected in series from the compressors 140 to the first row plurality of inflatable cushions 156a. In other embodiments, the first plurality of tubes 158a may be fluidly connected in parallel or other configurations. In some embodiments, the first plurality of tubes 158a or hoses are formed of a silicon material. In other embodiments, the first plurality of tubes 158a or hoses are formed of other materials that may include, without limitation, rubber, polyethylene, polyvinyl chloride, and/or the like.

In some embodiments, each of the plurality of honeycomb units 154a are configured as a constrained pneumatic flexible actuator that moves based on an inflation/deflation of a corresponding inflatable cushion of the first row plurality of inflatable cushions 156a. As such, each of the plurality of honeycomb units 154a include a cavity 160a that houses the corresponding inflatable cushion of the first row plurality of inflatable cushions 156a. In some embodiments, the cavity 160a may be reinforced by cuffed or embedded fibers, fabrics, or other fiber-like structures. Further, the cavity 160a and other portions of the plurality of honeycomb units 154a may be configured to be formed from fibers, fabrics, and the like, to have elastic properties. As such, the plurality of honeycomb units 154a have anisotropic mechanical properties such that based on the amount of air pressure within the corresponding inflatable cushion of the first row plurality of inflatable cushions 156a, each of the plurality of honeycomb units 154a constrain the cavity 160a to produce anisotropic expansion and deformation, thus achieving a specific form of deformation motion.

A second row plurality of inflatable cushions 156b are positioned to extend within the second row 152b such that the second row plurality of inflatable cushions 156b are generally positioned within a corresponding one of the plurality of honeycomb units 154b, which are formed in an accordion arrangement. A second plurality of tubes 158b or hoses are fluidly connected between each one of the second row plurality of inflatable cushions 156b and the corresponding honeycomb units 154b to manipulate or move the pneumatic honeycomb network 150, as discussed in greater detail herein. In some embodiments, the second plurality of tubes 158b may be fluidly connected in series from the compressor 140 to the second row plurality of inflatable cushions 156b. In other embodiments, the second plurality of tubes 158b may be fluidly connected in parallel or other configurations. In some embodiments, the second plurality of tubes 158b or hoses are formed of a silicon material. In other embodiments, the second plurality of tubes 158b or hoses are formed of other materials that may include, without limitation, rubber, polyethylene, polyvinyl chloride, and/or the like.

In some embodiments, each of the plurality of honeycomb units 154b are configured as a constrained pneumatic flexible actuator that moves based on an inflation/deflation of a corresponding inflatable cushion of the second row plurality of inflatable cushions 156b. As such, each of the plurality of honeycomb units 154b include a cavity 160b that houses the corresponding inflatable cushion of the second row plurality of inflatable cushions 156b. In some embodiments, the cavity 160b may be reinforced by cuffed or embedded fibers, fabrics, or other fiber-like structures. Further, the cavity 160b and other portions of the plurality of honeycomb units 154b may be configured to be formed from fibers, fabrics, and the like, to have elastic properties. As such, the plurality of honeycomb units 154b have anisotropic mechanical properties such that based on the amount of air pressure within the corresponding inflatable cushion of the second row plurality of inflatable cushions 156b, each of the plurality of honeycomb units 154b constrain the cavity 160b to produce anisotropic expansion and deformation, thus achieving a specific form of deformation motion.

In some embodiments, each of the first row plurality of inflatable cushions 156a and the second row plurality of inflatable cushions 156b may be formed from a polyurethane nylon fabric. In other embodiments, each of the first row plurality of inflatable cushions 156a and the second row plurality of inflatable cushions 156b may be formed from nylon, rubber, silicone, neoprene, and/or the like. It should be understood that the pneumatic honeycomb network 150 may be defined by first row plurality of inflatable cushions 156a and the second row plurality of inflatable cushions 156b, the first plurality of tubes 158a or hoses, the second plurality of tubes 158b or hoses, and the plurality of honeycomb units 154a, 154b.

In the depicted embodiment, illustrated is a pair of pneumatic honeycomb networks 150 that are positioned within the cavity 116 and external to the opening 136 of the at least one deflector member 132. That is, each of the pair of pneumatic honeycomb networks 150 are positioned and configured to make contact with the outer surface 138b of the at least one deflector member 132. As such, upon activation, each of the pneumatic honeycomb networks 150 may contact the outer surface 138b of the at least one deflector member 132 to further deform the at least one deflector member 132 by moving or manipulating at least one of the pair of side terminating surfaces 134c, and/or other parts or surfaces of the at least one deflector member 132, which in turn may manipulate, deform, or otherwise move the upper terminating surface 134a, the lower terminating surface 134b, other portions of the side terminating surfaces 134c, and/or the opening 136 and the inner surface 138a of the at least one deflector member 132.

That is, each of the pair of pneumatic honeycomb networks 150 are constrained by the cavity 116 of the seatback 114 such that upon activation, an exterior surface 162 of at least one of the plurality of honeycomb units 154a and/or the plurality of honeycomb units 154b of the pneumatic honeycomb networks 150 contacts the outer surface 138b of the at least one deflector member 132 to deform to the at least one deflector member 132. The deformation of the at least one deflector member 132 further changes the shape of the at least one fluid medium 130 in a predetermined manner to move the sensor 111, as best depicted in FIG. 3C. In response, there is improved acoustic detection by the sensor 111, improvements in capturing the plurality of heart sound waves 126 by reducing noise, and the like.

That is, during activation of the pneumatic honeycomb networks 150, when the first row plurality of inflatable cushions 156a and/or the second row plurality of inflatable cushions 156b inflate, the corresponding plurality of honeycomb units 154a, 154b will elongate under the action of the inflatable cushions, and the other side will deform less due to the restoring force of the plurality of honeycomb units 154a, 154b, respectively, such that the portions or the entire pneumatic honeycomb network 150 acts as an actuator to bend in the opposite direction. In addition, when both the inflatable cushions are inflated simultaneously, the pneumatic honeycomb networks will elongate. By controlling the combination of inflation of the first row plurality of inflatable cushions 156a and/or the second row plurality of inflatable cushions 156b, the pneumatic honeycomb network 150 may achieve multiple bending and elongation deformations. As such, during activation of the pneumatic honeycomb networks 150, the plurality of honeycomb units 154a, 154b generate robot moves through the folding-extension deformation of a plurality of honeycomb units 154a, 154b, causing structural deformation actuation by pneumatic honeycomb networks 150 to act as a soft arm member.

In the depicted embodiment, the sensor 111 is moved upon activation of at least one pneumatic honeycomb network of the pair of pneumatic honeycomb networks 150 in the vertical direction (e.g., in the +/−Z direction) to better position the sensor 111 with respect to the heart 124 of the occupant 123 and to better channel the acoustics in the at least one fluid medium 130 by the deformation of the at least one deflector member 132 to the sensor 111. This is non-limiting, upon activation of the at least one pneumatic honeycomb network of the pair of pneumatic honeycomb networks 150, the sensor 111 may be moved in any direction, including the longitudinal direction (e.g., in the +/−X direction), the lateral direction (e.g., in the +/−Y direction), the vertical direction (e.g., in the +/−Z direction), and/or combinations thereof, to better position the sensor with respect to the heart 124 of the occupant 123.

Additionally, in the depicted embodiment, the pneumatic honeycomb networks 150 are depicted as positioned within the cavity 116 of the seatback 114 on either side of the at least one deflector member 132. This is non-limiting and either or both of the pneumatic honeycomb networks 150 may be positioned anywhere along the at least one acoustic deflector between the outer surface of the at least one acoustic deflector and the surface of the seatback. Further, it should be understood that there may only be one pneumatic honeycomb network or more than two pneumatic honeycomb networks.

Further, in the depicted embodiment, the at least one actuation device is depicted as a pair of compressors. This is non-limiting and they may be one compressor or more than two compressors that are fluidly coupled to the pneumatic honeycomb networks. Further, in the depicted embodiment, the pair of compressors are depicted as positioned within the cavity of the seatback. This is non-limiting and each of the pair of compressors may be positioned anywhere within the vehicle, such as with the seat cushion, floorboard, and the like. Additionally, other at least one actuation devices may be utilized such as, without limitation, actuators, motors, fluid driven actuators, mechanically driven actuators, and/or the like.

Additionally, in the depicted embodiment, the pneumatic honeycomb networks 150 are depicted as positioned within the cavity 116 of the seatback 114 on either side of the at least one deflector member 132. This is non-limiting and either or both of the pneumatic honeycomb networks 150 may be positioned anywhere along the at least one deflector member 132 between the outer surface 138b of the at least one deflector member 132 and the inner surface 118b and/or the rear interior surface 120b of the seatback 114. Further, it should be understood that there may only be one pneumatic honeycomb network 150 or more than two pneumatic honeycomb networks 150.

It should also be understood that for illustrative purposes, one of the pair of pneumatic honeycomb networks 150 is depicted in the activated state while the other one of the pneumatic honeycomb networks 150 is depicted in an inactivated state. This is to simply illustrate for simplicity purposes that the activation of one of the pneumatic honeycomb networks 150 may deform the at least one deflector member 132 thereby deforming the at least one fluid medium 130. In response, the sensor 111 is further moved by the at least one fluid medium 130 to position the sensor 111 in an improved position to gather quality heart sounds from the occupant and the deformation of the at least one deflector member 132 may direct the sounds within the at least one fluid medium 130 to the sensor 111. As such, both the pneumatic honeycomb networks 150 may be activated to equal or varying degrees, one may be activated while the other is not, and/or the like, to provide customization of the deformation of the at least one deflector member 132 to increase the signal-to-noise ratio and to accommodate varying anatomy changes between occupants, as desired.

Figure 4A:
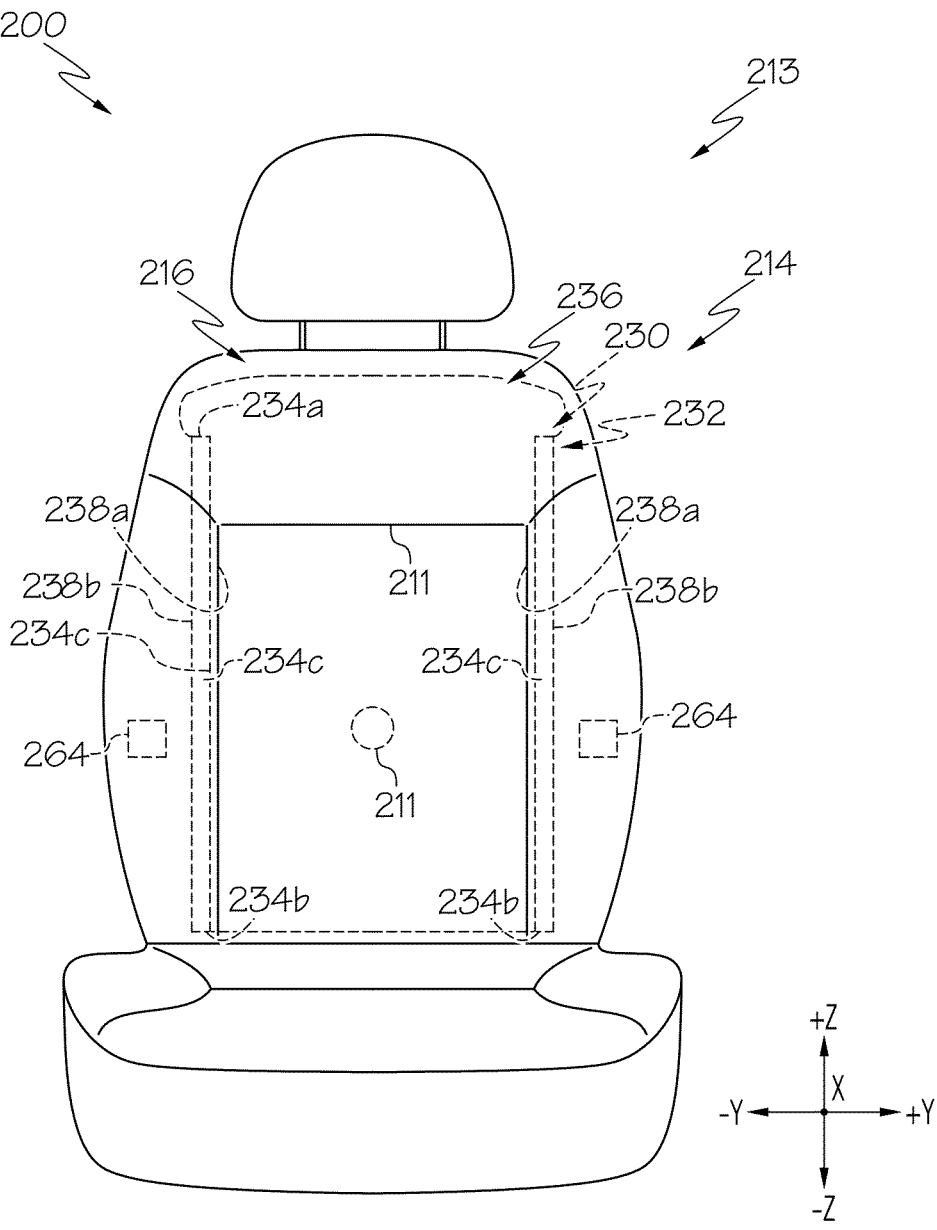
FIG. 4A schematically depicts a front plan view of a seat that includes a third aspect of a heart rate detection assembly depicted in an inactivated state, according to one or more embodiments shown and described herein.
Figure 4B:
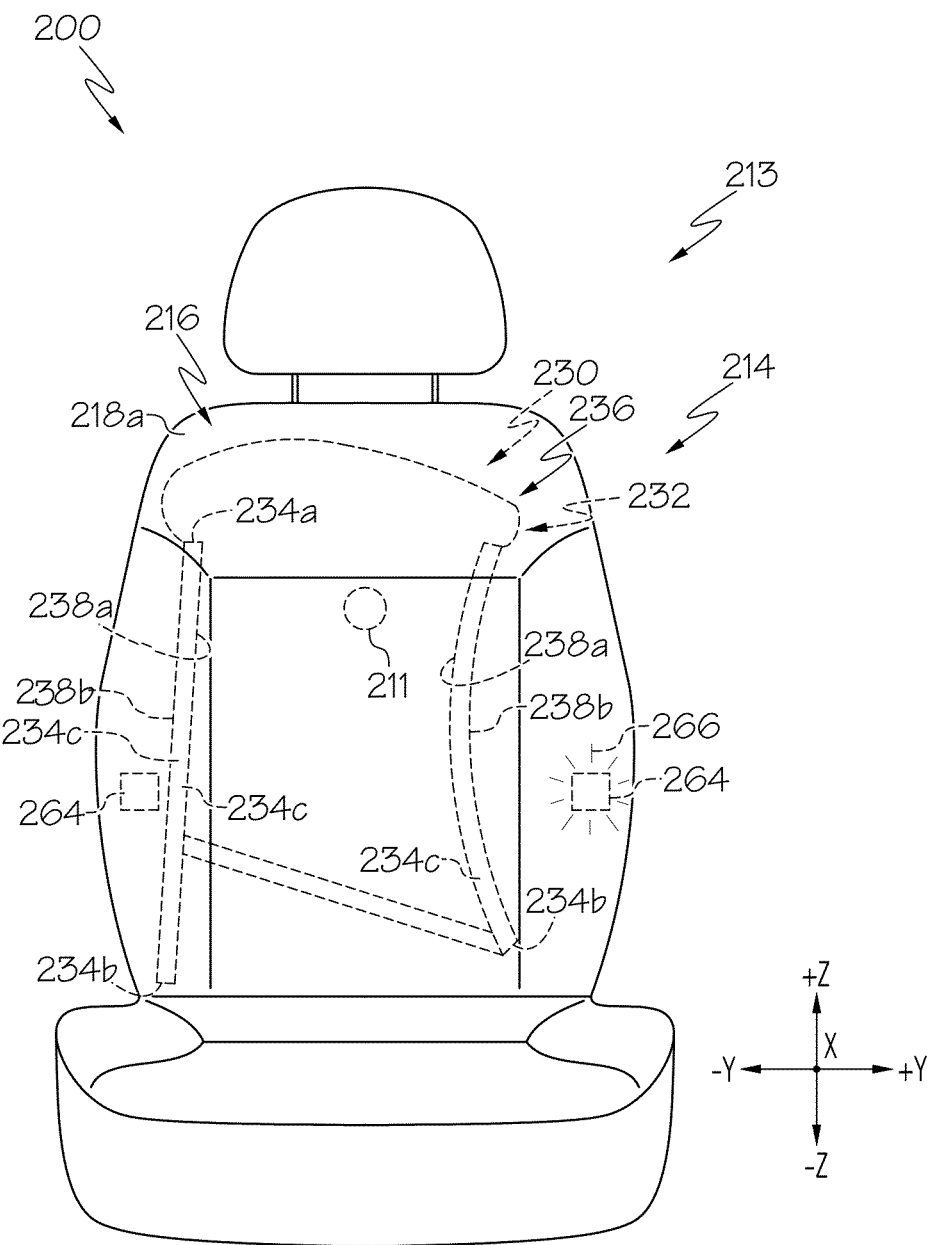
FIG. 4B schematically depicts the front plan view of the seat that includes the third aspect of the heart rate detection assembly of FIG. 4A depicted in a partially activated state, according to one or more embodiments shown and described herein.

Now referring to FIGS. 4A-4B, a third aspect of a heart rate detection device 200 is schematically depicted. It is understood that the heart rate detection device 200 is similar to the heart rate detection assembly 10 with the exceptions of the features described herein. As such, like features will use the same reference numerals with a prefix "2" for the reference numbers. For brevity reasons, these features will not be described again. Further, it should be understood that some or all reference characters are repeated in the description of FIGS. 4A-4B, but may not be specifically depicted in FIGS. 4A-4B.

In the depicted embodiment, the at least one actuation device is a pair of light sources 264 are positioned within the cavity 216 and external to the opening 236 of the at least one deflector member 232. That is, each of the pair of light sources 264 are positioned and configured to emit a light 266 that makes contact with the outer surface 238b of the at least one deflector member 232. As such, each of the pair of light sources 264 are configured to change between an activated state where a light is emitted, as best illustrated in FIG. 4B, and an inactivated state where light is not emitted, as best illustrated in FIG. 4A.

In these embodiments, the outer surface 238b of the at least one deflector member 232 may be reactive to the emittance of light from at least one of the pair of light sources 264 such that portions of the outer surface 238b deform in response to the emitted light 266. That is, in some embodiments, portions of the outer surface 238b of the at least one deflector member 232 may be coated in a material configured to bend or otherwise deform the portions of the outer surface 238b of the at least one deflector member 232. Example coatings include, without limitation, hydrogel, carbon materials, azobenzene, and/or the like. In other embodiments, the at least one deflector member 232 may be formed of materials that lead to deformation upon the contact with emitted light 266. For example, and without limitation, azobenzene-containing plastic film, natural polymer derivatives, polymers films, and/or the like.

As such, upon activation of at least one of the pair of light sources 264 portions of the outer surface 238b of the at least one deflector member 232 deform, as best illustrated in FIG. 4B. This deformation moves or manipulates at least one of the pair of side terminating surfaces 234c, and/or other parts or surfaces of the at least one deflector member 232. Such movement or deformation may manipulate, deform, or otherwise move the upper terminating surface 234a, the lower terminating surface 234b, other portions of the side terminating surfaces 234c, and/or the opening 236 and the inner surface 238a of the at least one deflector member 232. The deformation of the at least one deflector member 232 further changes the shape of the at least one fluid medium 230 in a predetermined manner to move the sensor 211, as best depicted in FIG. 4B. In response, there is improved acoustic detection by the sensor 211, improvements in capturing the plurality of heart sound waves 226 by reducing noise, and the like.

In the depicted embodiment, the sensor 211 is moved upon activation of at least one of the pair of light sources 264 in the vertical direction (e.g., in the +/−Z direction) to better position the sensor 211 with respect to the heart 224 of the occupant 223 and to better channel the acoustics in the at least one fluid medium 230 by the deformation of the at least one deflector member 232 to the sensor 211. This is non-limiting, upon activation of the least one of the pair of light sources 264, the sensor 211 may be moved in any direction, including the longitudinal direction (e.g., in the +/−X direction), the lateral direction (e.g., in the +/−Y direction), the vertical direction (e.g., in the +/−Z direction), and/or combinations thereof, to better position the sensor with respect to the heart 224 of the occupant 223.

Additionally, in the depicted embodiment, the pair of light sources 264 are positioned within the cavity 216 of the seatback 214 on either side of the at least one deflector member 232. This is non-limiting and either or both of the pair of light sources 264 may be positioned anywhere along the at least one deflector member 232 between the outer surface 238b of the at least one deflector member 232 and the inner surface 218b or the rear interior surface 220a of the seatback 214 or the inner surface 218b opposite of the occupant contact surface 218a. Further, it should be understood that there may only be one light source 264 or more than two light sources 264. Additionally, other at least one actuation devices may be utilized such as, without limitation, actuators, motors, fluid driven actuators, mechanically driven actuators, and/or the like.

It should also be understood that for illustrative purposes, one of the pair of light sources 264 is depicted in the activated state while the other one of the light sources 264 is depicted in an inactivated state. This is to simply illustrate for simplicity purposes that the activation of one of the light sources 264 may be configured to deform the at least one deflector member 232 thereby deforming the at least one fluid medium 230. In response, the sensor 211 is further moved by the at least one fluid medium 230 to position the sensor 211 in an improved position to gather quality heart sounds from the occupant and the deformation of the at least one deflector member 232 may direct the sounds within the at least one fluid medium 230 to the sensor 211. As such, either or both of the light sources 264 may be activated to equal or varying degrees or amounts of emitted light 266, one may be activated while the other is not, and the like, to provide customization of the deformation of the at least one deflector member 232 to increase the signal-to-noise ratio and to accommodate varying anatomy changes between occupants, as desired.

Each of the pair of light sources 264 may be communicatively coupled to the electronic control unit 12 (FIG. 7) such that the electronic control unit 12 (FIG. 7) may control each one of the pair of light sources 264, and the activation or inactivation of each of the light sources 264 necessary to change or manipulate the positioning of the at least one fluid medium 230 within the opening 236 of the at least one deflector member 232 and to direct the plurality of heart sound waves 226 to the sensor 211 by the deformation of the at least one deflector member 232.

Figure 5A:
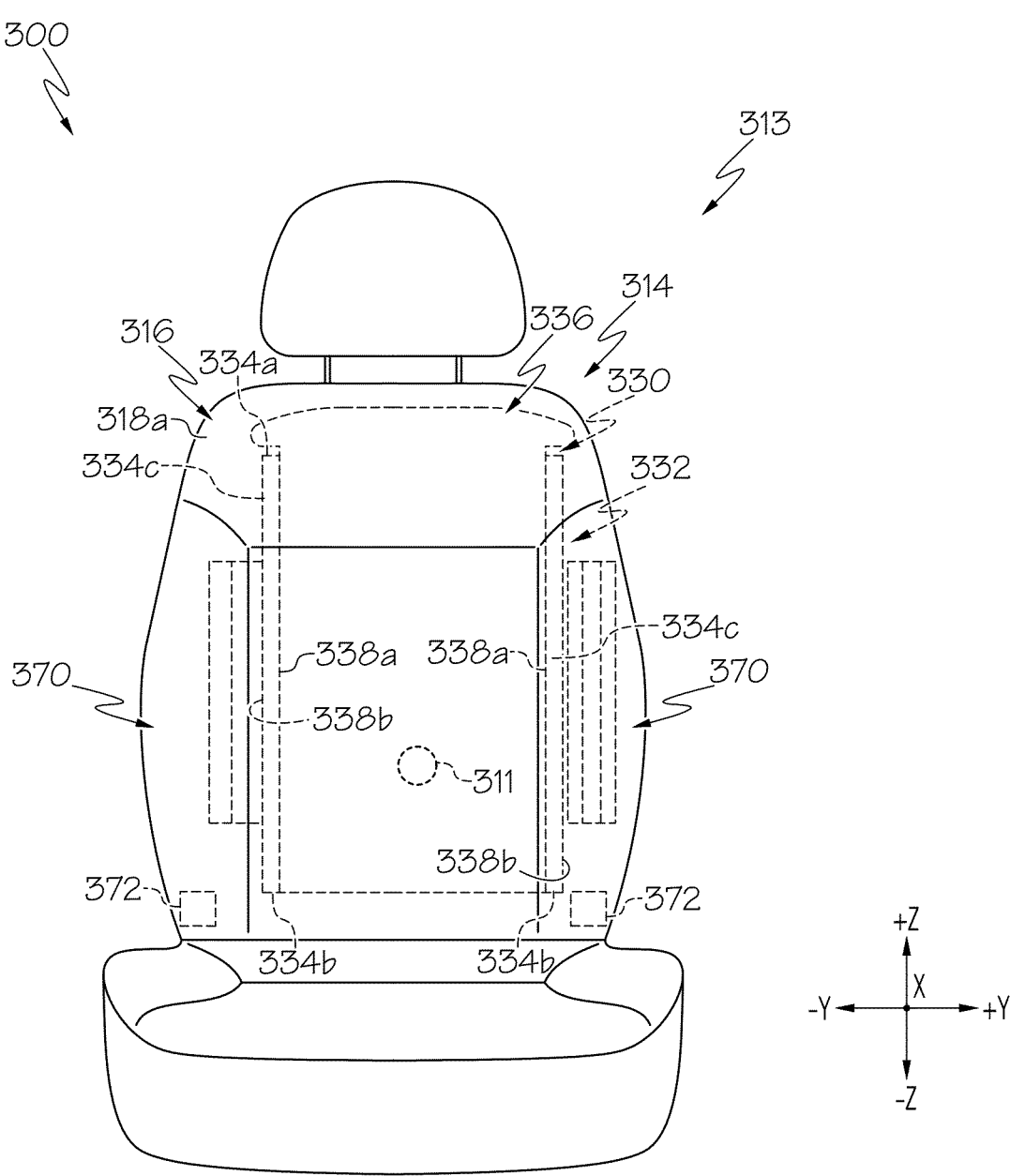
FIG. 5A schematically depicts a front plan view of a seat that includes a fourth aspect of a heart rate detection assembly depicted in an inactivated state, according to one or more embodiments shown and described herein.
Figure 5B:
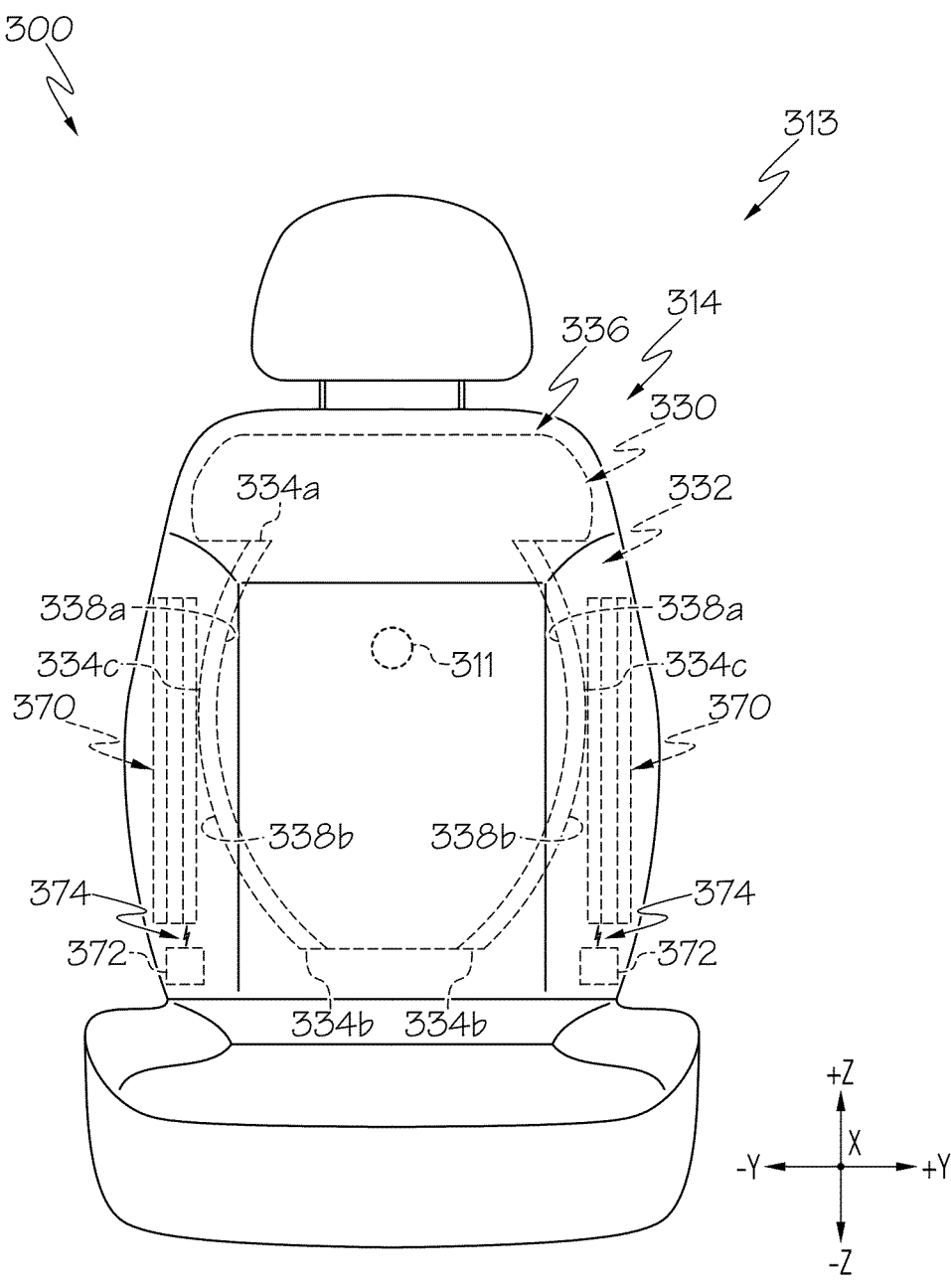
FIG. 5B schematically depicts the front plan view of the seat that includes the fourth aspect of the heart rate detection assembly of FIG. 4A depicted in a partially activated state, according to one or more embodiments shown and described herein.

Now referring to FIGS. 5A-5B, a fourth aspect of a heart rate detection device 300 is schematically depicted. It is understood that the heart rate detection device 300 is similar to the heart rate detection assembly 10 with the exceptions of the features described herein. As such, like features will use the same reference numerals with a prefix "3" for the reference numbers. For brevity reasons, these features will not be described again. Further, it should be understood that some or all reference characters are repeated in the description of FIGS. 5A-5B, but may not be specifically depicted in FIGS. 5A-5B.

In the depicted embodiment, the at least one deflector member 332 is configured to include a plurality of high voltage sheets 370 that may cause the at least one deflector member 332 to deform in a predetermined manner. That is, in this embodiment, the at least one deflector member 332 may act as an electrostatic mechanism actuator. Each of the plurality of high voltage sheets 370 and/or a combination of sheets may be configured to change between an activated state where a voltage is received and in response, the plurality of high voltage sheets 370 act as an actuator to deform the at least one deflector member 332, as best illustrated in FIG. 5B, and an inactivated state, where voltage is not received and there is not an active actuator mechanism to deform the at least one deflector member 332, as best illustrated in FIG. 5A. In some embodiments, a pair of voltage sources 372 are positioned within the cavity 316 and external to the opening 336 of the at least one deflector member 332. Each of the pair of voltage sources 372 are positioned and configured to transmit a voltage 374 to some or all of the plurality of high voltage sheets 370 thereby activating or inactivating selected sheets of the plurality of high voltage sheets 370. As such, each of the pair of voltage sources 372 are configured to change between a voltage-on state where a voltage is emitted to cause the plurality of high voltage sheets 370 to act as an actuator, as best illustrated in FIG. 5B, and a voltage-off state where voltage is not emitted thereby the plurality of high voltage sheets 370 is not an active actuator mechanism, as best illustrated in FIG. 5A.

In these embodiments, the outer surface 338b of the at least one deflector member 332 may be reactive to the emittance of voltage 374. That is, in some embodiments, at least one of the plurality of high voltage sheets 370 may be coupled to the outer surface 338b of the at least one deflector member 332. In other embodiments, the outer surface 338b of the at least one deflector member 332 may have embedded within at least one of the plurality of high voltage sheets 370. As such, when the plurality of high voltage sheets 370 act as an electrode, the sheet of the plurality of high voltage sheets 370 embedded within or coupled to the at least one deflector member 332 deforms or bends portions of the at least one deflector member 332, as best illustrated in FIG. 5B. This deformation moves or manipulates at least one of the pair of side terminating surfaces 334c, and/or other parts or surfaces of the at least one deflector member 332. Such movement or deformation may manipulate, deform, or otherwise move the upper terminating surface 334a, the lower terminating surface 334b, other portions of the side terminating surfaces 334c, and/or the opening 336 and the inner surface 338a of the at least one deflector member 332. The deformation of the at least one deflector member 332 further changes the shape of the at least one fluid medium 330 in a predetermined manner to move the sensor 311, as best depicted in FIG. 5B. In response, there is improved acoustic detection by the sensor 311, improvements in capturing the plurality of heart sound waves 326 by reducing noise, and the like.

In the depicted embodiment, the sensor 311 is moved due to the deformation of the at least one deflector member 332 upon activation of at least one of the pair of voltage sources 372. The sensor 311 may be guided or moved in the vertical direction (e.g., in the +/−Z direction) to better position the sensor 311 with respect to the heart 324 of the occupant 323 and to better channel the acoustics in the at least one fluid medium 330 by the deformation of the at least one deflector member 332 to the sensor 311. This is non-limiting, upon activation of the least one of the pair of voltage sources 372, the sensor 311 may be moved in any direction, including the longitudinal direction (e.g., in the +/−X direction), the lateral direction (e.g., in the +/−Y direction), the vertical direction (e.g., in the +/−Z direction), and/or combinations thereof, to better position the sensor 311 with respect to the heart 324 of the occupant 323.

Additionally, in the depicted embodiment, the pair of voltage sources 372 are positioned within the cavity 316 of the seatback 314 on either side of the at least one deflector member 332. This is non-limiting and either or both of the pair of voltage sources 372 may be positioned anywhere in the vehicle such as within the seat cushion, floorboard, engine compartment, and the like. Further, it should be understood that there may only be one voltage source 372 or more than two voltage sources 372. Additionally, other at least one actuation devices may be utilized such as, without limitation, actuators, motors, fluid driven actuators, mechanically driven actuators, and/or the like.

It should also be understood that for illustrative purposes, both sets of the plurality of high voltage sheets 370 are illustrated in an activated state in FIG. 5B. This is non-limiting and in embodiments, only one of the sets of the plurality of high voltage sheets 370 may be activated. As such, some, or all of the plurality of high voltage sheets 370 may be activated to equal or varying degrees of emitted voltages 374, one may be activated while the other is not, and the like, to provide customization of the deformation of the at least one deflector member 332 to increase the signal-to noise ratio and to accommodate varying anatomy changes between occupants, as desired.

Each of the pair of voltage sources 372 may be communicatively coupled to the electronic control unit 12 (FIG. 7) such that the electronic control unit 12 (FIG. 7) may control each one of the pair of voltage sources 372, and the activation or inactivation of each of the voltage sources 372 necessary to change or manipulate the positioning of the at least one fluid medium 330 within the opening 336 of the at least one deflector member 332 and to direct the plurality of heart sound waves 326 to the sensor 311 by the deformation of the at least one deflector member 332.

Figure 8:
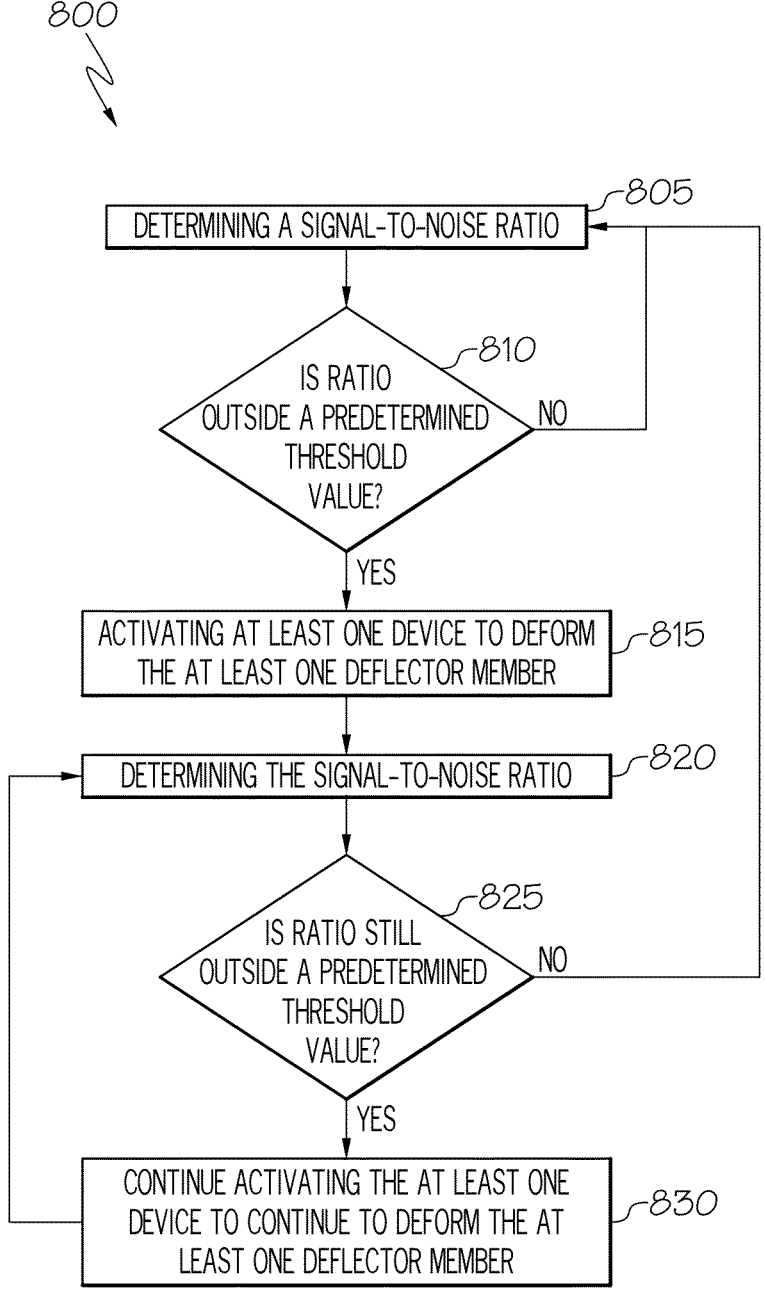
FIG. 8 is an illustrative flow diagram of a method for improving a signal-to-noise ratio of a plurality of heart sound waves from an occupant within a seat of a vehicle, according to one or more embodiments shown and described herein.

Turning now to FIG. 8, an illustrative flow diagram of an illustrative method 800 of improving a signal-to-noise ratio of a plurality of heart sound waves from an occupant within a seat of a vehicle is provided. Although the steps associated with the blocks of FIG. 8 will be described as being separate tasks, in other embodiments, the blocks may be combined or omitted. Further, while the steps associated with the blocks of FIG. 8 will be described as being performed in a particular order, in other embodiments, the steps may be performed in a different order.

At block 805, when the occupant is positioned within the seat, a current signal-to-noise ratio is determined. It should be understood that the signal-to-noise ratio is a contactless measurement of the plurality of heart sound waves from the heart of the occupant sitting in the seat detected by the sensor and is a comparison of a level of a desired signal to a level of background noise. At block 810, the current signal-to-noise ratio is compared to a predetermined threshold value and a determination is made whether the current signal-to-noise ratio is outside of the predetermined threshold level or range. The predetermined threshold level or range may be a minimum desirable signal-to-noise ratio, a maximum desirable signal-to-noise ratio, or some values therebetween. Further, outside of the predetermined threshold level or range may mean above or below the predetermined threshold level or range or below the minimum desirable signal-to-noise ratio, above the maximum desirable signal-to-noise ratio, or some undesirable values therebetween. When the current signal-to-noise ratio is not outside the predetermined threshold value or range, the method 800 loops between blocks 805 and 810.

When the current signal-to-noise ratio is outside of the predetermined threshold value, at block 815, at least one device is activated to deform the at least one deflector member. As such, the at least one deflector member may be selectively deformed when desirable. Further, the amount or degree of deformation may be variable. It should be appreciated that the method 800 may be iterative and thus the deformation of the at least one deflector member may be in varying degrees. The at least one device may be a compressor, light source, voltage source, and/or the like, that is configured to work either by itself or in conjunction with other devices (e.g., inflatable cushion, pneumatic honeycomb network, light responsive material, plurality of high voltage sheets, and the like) to deform the at least one deflector member. At block 820, a new, current signal-to-noise ratio is determined. It should be understood that the signal-to-noise ratio may now be changed due to the deformation of the at least one deflector member, which may have moved or relocated the sensor and/or may be channeling the plurality of heart sounds in an improved manner to the sensor.

At block 825, the new, current signal-to-noise ratio is compared to the predetermined threshold value or range and a new determination is made whether the new, current signal-to-noise ratio remains outside of the predetermined threshold level or range. When the current signal-to-noise ratio is not outside the predetermined threshold value or range, the method 800 loops back to block 805 and proceeds to loop between blocks 805 and 810, as discussed in greater detail above.

When the current signal-to-noise ratio remains outside of the predetermined threshold value or range, at block 830, the at least one device is continued to be activated to further deform the at least one deflector member. Again, it should be appreciated that the deformation may be at small increments, larger increments, or some value therebetween based on the current signal-to-noise ratio and the predetermined threshold value or range. Further, following the continued activation of the at least one device at block 830, a new, current signal-to-noise ratio is determined at block 820, and the new, current signal-to-noise ratio is compared to the predetermined threshold value or range and a new determination is made whether the new, current signal-to-noise ratio remains outside of the predetermined threshold level or range, at block 825. As such, blocks 820-830 may continuously loop until there is a determination, at block 825, that the current signal-to-noise ratio is not outside the predetermined threshold value or range, the method 800 loops back to block 805 and proceeds to loop between blocks 805 and 810, as discussed in greater detail above.

It should now be understood that embodiments of the present disclosure are directed to heart rate detection devices positioned within seats of vehicles that are configured to increase signal-to-noise ratio by providing a sensor that is movable and customizable based on an anatomy of the occupant positioned within the seat while improving the quality of detecting a plurality of heart sounds by deforming at least one deflector member to channel the plurality of heart sounds to the sensor.

While particular embodiments have been illustrated and described herein, it should be understood that various other changes and modifications may be made without departing from the scope of the claimed subject matter. Moreover, although various aspects of the claimed subject matter have been described herein, such aspects need not be utilized in combination. It is therefore intended that the appended claims cover all such changes and modifications that are within the scope of the claimed subject matter.

It will be apparent to those skilled in the art that various modifications and variations can be made to the embodiments described herein without departing from the scope of the claimed subject matter. Thus, it is intended that the specification cover the modifications and variations of the various embodiments described herein provided such modification and variations come within the scope of the appended claims and their equivalents.

What is claimed is:

1. A system to identify a signal-to-noise ratio of a plurality of heart sound waves within a vehicle seat, the system comprising:

a sensor positioned within a cavity of the vehicle seat;

at least one fluid medium positioned within the cavity; and at least one deflector member positioned within the cavity, the at least one deflector member at least partially surrounding the at least one fluid medium such that the at least one deflector member is configured to constrain and direct the plurality of heart sound waves through the at least one fluid medium to the sensor when an occupant is positioned within the vehicle seat, the at least one deflector member is configured to selectively deform to channel the plurality of heart sound waves to the sensor;

at least one actuation device positioned within the cavity;

a processor communicatively coupled to the at least one actuation device; and a non-transitory, processor-readable storage medium in communication with the processor, the non-transitory, processor-readable storage medium comprising one or more programming instructions that, when executed, cause the processor to:

obtain the signal-to-noise ratio of the plurality of heart sound waves, determine that the signal-to-noise ratio is not at a predetermined threshold, and in response, actuate the at least one actuation device to deform the at least one deflector member.

2. The system of claim 1, wherein the at least one actuation device is a compressor.

3. The system of claim 2, further comprising:

at least one inflatable cushion positioned within the cavity, the at least one inflatable cushion is configured to be fluidly coupled to the compressor, the at least one inflatable cushion is configured to change between a deflated state where the at least one deflector member is not deformed, and an inflated state where the at least one deflector member is deformed.

4. The system of claim 1, wherein the at least one actuation device is a light source configured to emit a light when the light source is in an activated state and does not emit the light when the light source is in an inactivated state.

5. The system of claim 4, wherein the at least one deflector member is configured to deform when the light source is in the activated state.

6. The system of claim 1, wherein the at least one actuation device is a voltage source configured to emit a voltage when the voltage source is in a voltage-on state and does not emit the voltage when the voltage source is in a voltage-off state.

7. The system of claim 6, further comprising:

a plurality of high voltage sheets positioned within the cavity and configured to move when the voltage source is in the voltage-on state and static when the voltage source is in the voltage-off state, wherein the at least one deflector member is deformed when the plurality of high voltage sheets move in response to the voltage source in the voltage-on state.

8. A method for improving a signal-to-noise ratio of a plurality of heart sound waves from an occupant within a seat of a vehicle, the method comprising:

obtaining the signal-to-noise ratio of the plurality of heart sound waves, the plurality of heart sound waves obtained via a sensor positioned within at least one fluid medium positioned within a cavity of the seat;

determining that the signal-to-noise ratio is not at a predetermined threshold, and in response, actuating at least one actuation device that is configured to deform at least one deflector member, the at least one deflector member positioned within the cavity, the at least one deflector member at least partially surrounding the at least one fluid medium such that the at least one deflector member is configured to constrain and direct the plurality of heart sound waves through the at least one fluid medium to the sensor.

9. The method of claim 8, wherein a shape of the at least one fluid medium changes in response to an anatomy of the occupant positioned in the seat.

10. The method of claim 9, wherein in response to the change in shape of the at least one fluid medium, the sensor moves to optimize a location of the sensor based on the anatomy of the occupant positioned in the seat.

* * * * *